(12) United States Patent
Keijzer

(10) Patent No.: US 9,914,971 B2
(45) Date of Patent: Mar. 13, 2018

(54) TREATMENT AND BIOMARKER FOR PULMONARY HYPOPLASIA IN CONGENITAL DIAPHRAGMATIC HERNIA

(71) Applicant: University of Manitoba, Winnipeg (CA)

(72) Inventor: Richard Keijzer, Winnipeg (CA)

(73) Assignee: University of Manitoba, Winnipeg, Manitoba (CA)

(*) Notice: Subject to any disclaimer, the term of this patent is extended or adjusted under 35 U.S.C. 154(b) by 0 days.

(21) Appl. No.: 15/514,654

(22) PCT Filed: Oct. 9, 2015

(86) PCT No.: PCT/CA2015/051028
§ 371 (c)(1),
(2) Date: Mar. 27, 2017

(87) PCT Pub. No.: WO2016/054747
PCT Pub. Date: Apr. 14, 2016

(65) Prior Publication Data
US 2017/0240970 A1   Aug. 24, 2017

Related U.S. Application Data

(60) Provisional application No. 62/062,459, filed on Oct. 10, 2014.

(51) Int. Cl.
*A61K 48/00*     (2006.01)
*C12Q 1/68*      (2018.01)
*C12N 15/113*    (2010.01)

(52) U.S. Cl.
CPC .......... *C12Q 1/6883* (2013.01); *C12N 15/113* (2013.01); *C12N 2310/113* (2013.01); *C12N 2310/141* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2012/0282326 A1* 11/2012 Chakrabarti ....... A61K 31/7088
                                                          424/450

OTHER PUBLICATIONS

Periera-Terra P. et al Unique tracheal fluid micro RNA signature predicts response to FETO in patients with congenital diaphragmatic hernia. Annals of Surgery 2015, 262(6): 1130-1140, ISSN 0003-4932.
Castilla, M.A. et al, Micro-RNA signature of the epithelial-mesenchymal transition in endometrial carcinosarcoma. Journal of Pathology, 2011,223(1): 72-80 ISSN 0022-3417.
Veerla S. et al MiRNA expression in urothelial carcinomas: Important role of miR-10a, miR-222, miR-125b, miR-7 and miR-452 for tumor stage and metastasis and frequent homozygous losses of miR-31, Int. J. Cancer 2009 124:2236-2242 ISSN.
Marimuthu, A. et al Identification of targets of miR-200b by a SILAC-based quantitative proteomic approach EuPA Open Proteomics, 2014 4:10-17, ISSN 2212-9685.

* cited by examiner

*Primary Examiner* — Kimberly Chong
(74) *Attorney, Agent, or Firm* — Michael R. Williams; Ryan W. Dupuis; Ade & Company Inc.

(57) ABSTRACT

Congenital diaphragmatic hernia (CDH) is a developmental defect of the diaphragm, causing abdominal viscera to herniate into the thorax. A common genetic cause for CDH and the associated abnormal lung development has not been identified. We have found that human fetal hypoplastic CDH lungs have a specific microRNA miR-200/miR-10a signature, which changes in response to fetal therapy.

3 Claims, 19 Drawing Sheets

*Figure 6A*: miR-200b expression (qRT-PCR) is dynamic during normal rat lung development.

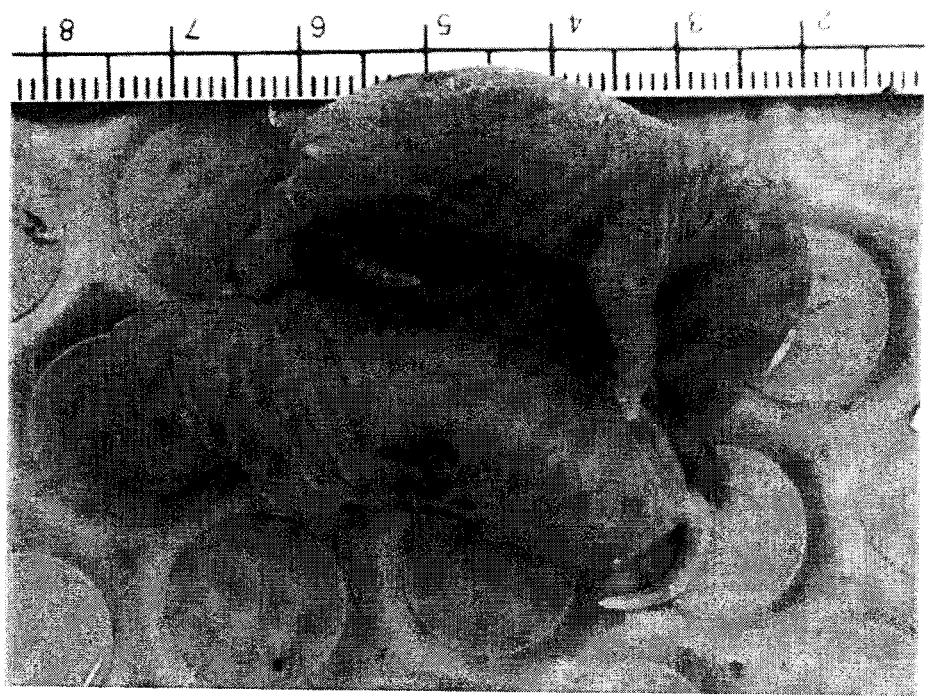
Figure 9A: panel B
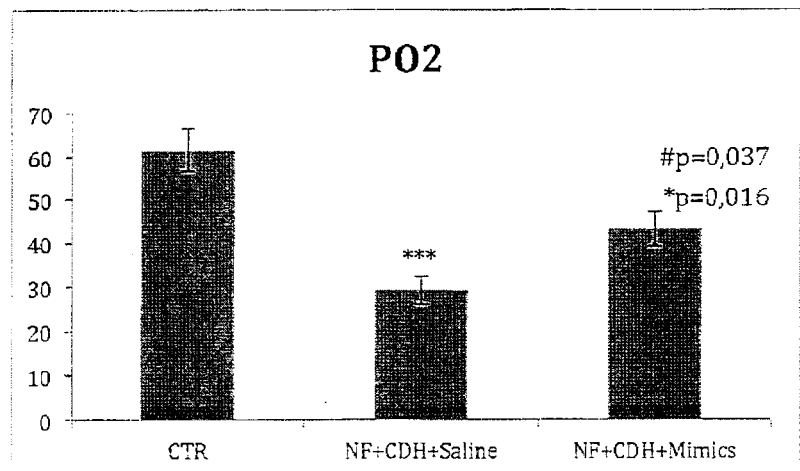
A
CTR n=7; NF+CDH+Saline n=11; NF+CDH+Mimics n=14
Bonferroni t-test * vs CTR # vs NF+CDH+Saline g

TREATMENT AND BIOMARKER FOR PULMONARY HYPOPLASIA IN CONGENITAL DIAPHRAGMATIC HERNIA

PRIOR APPLICATION INFORMATION

The instant application claims the benefit of U.S. Provisional Patent Application, Ser. No. 62/062,459, filed Oct. 10, 2014 entitled 'Treatment and Biomarker for Pulmonary Hypoplasia in Congenital Diaphragmatic Hernia, the contents of which are incorporated herein by reference.

BACKGROUND OF THE INVENTION

Congenital diaphragmatic hernia (CDH) is a developmental defect of the diaphragm, allowing herniation of abdominal viscera into the chest. It occurs in 1 in 2,000 to 3,000 live births (1). Although the postnatal treatment has become more standardized, substantial morbidity and mortality result from the associated pulmonary hypoplasia and abnormal vascular development of the newborn. A subset of fetuses with liver herniation and a smaller lung size, represented by an observed over expected lung-to-head ratio (O/E LHR) under 25%, have higher mortality and morbidity rates and currently are offered in utero fetal surgery. Fetoscopic endoluminal tracheal occlusion (FETO) (2) prevents normal egress of airway fluid, which in turn induces tissue stretch, acting as a signal for lung growth. A lack of understanding of the molecular mechanisms underlying pulmonary hypoplasia in CDH hampers progress for potential in utero therapies and case selection. A common genetic cause for CDH is unknown (7). However, it is widely accepted that the diaphragmatic defect and pulmonary hypoplasia result from a shared developmental insult (8, 9).

MicroRNAs (miRNAs) are small non-coding RNAs that regulate gene expression through post-transcriptional silencing of messenger RNAs (10). MicroRNAs are essential for normal organogenesis during embryonic development. For example, targeted deletion of miR-1-2 leads to congenital heart defects in mice (11). Previous studies have identified differential miRNA expression between various stages of lung development, but these studies did not provide much functional information (12). Whether specific miRNAs play a role in the pathogenesis of human congenital lung diseases remains unknown. Isolated CDH is characterized by abnormal lung development and may therefore serve as a template to study molecular mechanisms driving lung growth and differentiation. The prenatal period offers a unique clinical research opportunity, since CDH cases can now be well characterized by prenatal imaging and postnatal outcome.

Only about 15%-20% of individuals with CDH have been identified with chromosome abnormalities or a single gene disorder and in all these patients, CDH occurred with additional malformations (complex-CDH) (71, 72). The etiology of the remaining 80%-85% (isolated-CDH) is currently unknown. Little is known about the role of specific miRNAs during lung development and it appears that different groups of miRNAs can regulate different stages of lung development. Most research studies in lung morphology and organogenesis are limited in comparing expression profiles of miRNAs at various stages of lung development (75). The miR-200 family is comprised of five members which are transcribed in two clusters: miR-200b, 200a and 429 share a common transcription start site on chromosome 1, while miR-200c and 141 are transcribed as a single unit from chromosome 12(76). MiR-200 family members are considered as epithelial markers and can revert an epithelial-mesenchymal transition (EMT) in cancer and pulmonary fibrosis by directly targeting two transcription factors, ZEB1 and ZEB2(77, 32, 78, 79). However, the functional role of miR-200b in normal lung development and hypoplastic lung resulting from CDH is currently unknown.

The elegant nitrofen rat model has been widely used to investigate the patho-physiological mechanisms of abnormal lung development associated with CDH. Moreover, it has direct resemblance because of its striking similarities to human CDH, such as liver herniation, a large diaphragmatic defect, and asymmetrical lung hypoplasia and pulmonary hypertension (70).

SUMMARY OF THE INVENTION

According to an aspect of the invention, there is provided a method of determining if a patient has abnormal lung development due to congenital diaphragmatic hernia comprising of: measuring levels of miR-200b microRNA and/or miR-10a microRNA in a sample from said patient, wherein if the levels of the miR-200b or the miR-10a in the sample are significantly upregulated as compared to an average control level, the patient suffers from abnormal lung development.

According to another aspect of the invention, there is provided a method of predicting success of prenatal tracheal occlusion for treatment of abnormal lung development due to congenital diaphragmatic hernia in a patient comprising: measuring levels of at least one of the miR-200 microRNA family members and/or miR-10a microRNA in a sample from said patient, wherein if the levels of one of the miR-200 microRNA family members or the miR-10a microRNA in the sample are not significantly upregulated in the tracheal fluid sample at the moment of balloon removal compared to an average control level or as compared to what these levels were when the balloon was placed, the patient is at risk of not surviving after birth.

According to a further aspect of the invention, there is provided a method of treating or preventing abnormal lung development in Congenital Diaphragmatic Hernia (CDH) comprising of: administering to an individual in need of such treatment an effective amount of a miR-200b modulating compound.

Finally, evidence is provided that miR-200b is an important component in the pathogenesis of adult lung fibrosis.

BRIEF DESCRIPTION OF THE DRAWINGS

FIG. 9A. Preliminary gasometric analysis shows improved oxygen levels in nitrofen fetuses treated with 5 mg/kg miR-200b mimics in utero (A). We also noticed improved oxygenation in newborn nitrofen fetuses following 5 mg/kg miR-200b mimics treatment in utero (B, top).

DESCRIPTION OF THE PREFERRED EMBODIMENTS

Figure 1:
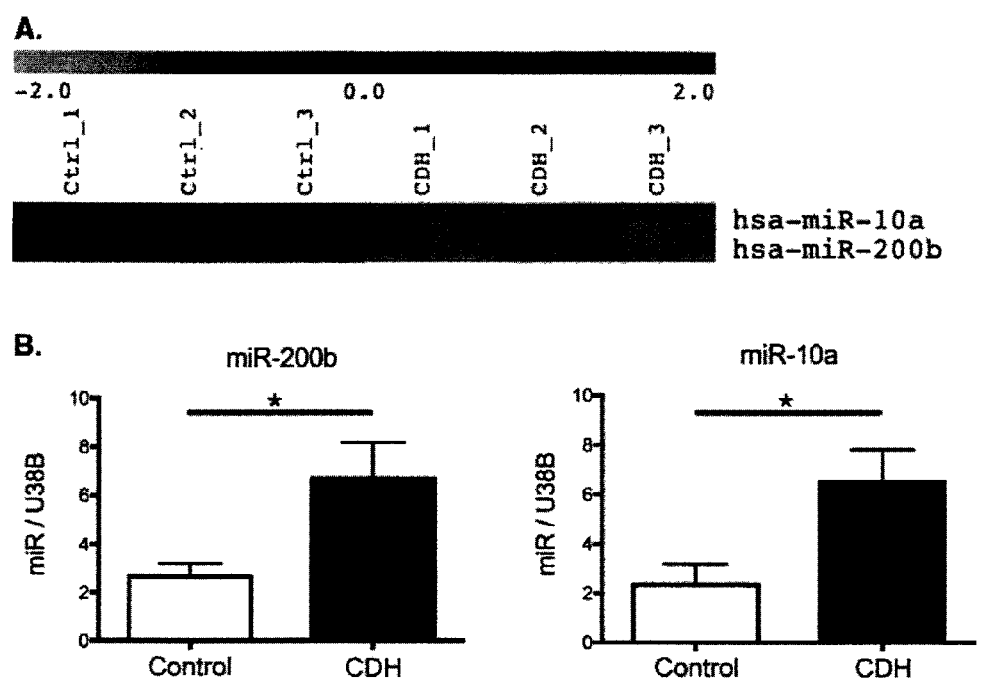
FIG. 1. Upregulation of miR-200b and miR-10a in prenatal lungs in congenital diaphragmatic hernia (CDH). Total RNA was extracted from 3 CDH cases and 3 age-matched controls (Ctrl). (A) Heat map representation of normalized microarray data (log 2 scale). Of the 319 miRNAs tested, miR-200b and miR-10a were overexpressed in hypoplastic lungs (P<0.01). (B) Real-time PCR confirmed overexpression of miR-200b and miR-10a in CDH (*P<0.05). miRNA expression is normalized relative to SNORD38B (U38B).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The first objective was to determine whether severe human hypoplastic CDH lungs display specific microRNA expression. The second objective was to determine if the obtained microRNA signature could be used as a biomarker, by evaluating its expression in tracheal and amniotic fluid samples of CDH patients before and after forced lung growth. The third objective was to determine how abnormal miR-200b expression influences target gene expression.

This is the first study to identify abnormal miR-200/miR10a expression in hypoplastic CDH lungs and in response to forced lung growth. The expression of these microRNAs in tracheal fluid can be used to distinguish survivors of FETO from non-survivors. We also demonstrate that increased miR-200b expression results in decreased target gene expression via decreased TGF-β/SMAD signaling.

We also address the potential role of miR-200b in regulating the lung development through the suppression of TGF-β/ SMAD signaling and define a unique mechanism by which the TGF-β/ SMAD signaling pathway is inhibited in CDH. An improved understanding of miR-200b role in normal and abnormal lung development is likely to suggest new therapies & prognostic biomarkers for the treatment of lung anomalies especially congenital diaphragmatic hernia.

According to an aspect of the invention, there is provided a method of determining if a patient has abnormal lung development due to congenital diaphragmatic hernia comprising: measuring levels of miR-200b microRNA and/or miR-10a microRNA in a sample from said patient, wherein if the levels of the miR-200b or the miR-10a in the sample are significantly upregulated as compared to an average control level in a similar sample from individuals of the same age with no disease of the lung, the patient suffers from abnormal lung development.

As will be appreciated by one of skill in the art, the patient is an individual who has been identified as potentially having or being at risk of having abnormal lung development, for example, as a result of a structural ultrasound scan. It is of note that such individuals are typically of 18-20 weeks gestational age when the structural ultrasound scan is carried out.

Accordingly, as will be appreciated by one of skill in the art, the "average control level" may be determined by a variety of means, for example by measuring levels of miR-200b microRNA and/or miR-10a microRNA from individuals of the same approximate age who showed normal lung development in the structural ultrasound. The expression levels measured would then be averaged using any of a variety of means known in the statistical arts. It is of note that the specific value will of course depend on a variety of factors, for example, the sample source and the detection method used.

As will be appreciated by one of skill in the art, the average control test does not need to be repeated each time and may be considered to be a threshold value. Any level of miR-200b or miR-10a above the average control level may be considered to be an indication of abnormal lung development. However, in some embodiments, the levels are considered to be upregulated if the sample is displaying miR-200b or miR-10a expression at least two times or at least three times higher than the average control sample.

The sample may be any suitable sample, for example but by no means limited to amniotic fluid, tracheal fluid, blood, cord blood, lung tissue, diaphragm tissue or induced pluripotent stem cells derived from patient's skin fibroblasts.

The levels may be measured by a suitable means known in the art, for example but by no means limited to a method selected from the group consisting of: microRNA reverse transcription quantitative polymerase chain reaction (RT-qPGR), semi-quantitative in situ hybridization and Northern blotting.

According to another aspect of the invention, there is provided a method of predicting success of prenatal tracheal occlusion for treatment of abnormal lung development due to congenital diaphragmatic hernia in a patient comprising: measuring levels of one of the miR-200microRNA family members and/or miR-10a microRNA in a sample from said patient, wherein if the levels of one of the miR-200 microRNA family members and/or miR-10a microRNA in the sample are not significantly upregulated in the tracheal fluid sample at the moment of balloon removal, as compared to what these levels were when the balloon was placed or as compared to the average control level, the patient is at risk of not surviving after birth.

As will be appreciated by one of skill in the art, the average control test does not need to be repeated each time and may be considered to be a threshold value. Any level of miR-200b or miR-10a above the average control level may be considered to be an indication of abnormal lung development. However, in some embodiments, the levels are considered to be upregulated if the sample is displaying miR-200b or miR-10a expression at least two times or at least three times higher than the average control sample.

The levels may be measured by any suitable means known in the art, for example but by no means limited to a method selected from the group consisting of: microRNA reverse transcription quantitative polymerase chain reaction (RT-qPCR), semi-quantitative in situ hybridization and Northern blotting.

The sample may be any suitable sample, for example but by no means limited to amniotic fluid, tracheal fluid, blood, cord blood, lung tissue, diaphragm tissue or induced pluripotent stem cells derived from patient's skin fibroblasts.

According to a further aspect of the invention, there is provided a method of treating or preventing abnormal lung development in Congenital Diaphragmatic Hernia (CDH) comprising: administering to an individual in need of such treatment an effective amount of a miR-200b modulating compound.

An individual in need of such treatment is an individual who has been diagnosed with or is at risk of developing CDH, for example, an individual who has been identified as possibly having abnormal lung development during a structural ultrasound. It is of note that such an individual is typically of 18-20 weeks gestational age.

As will be appreciated by one of skill in the art, a miR-200b modulating compound as used herein refers to any compound able to increase miR-200b expression, for example, a miR-200b mimic—a non-natural double stranded microRNA-like RNA fragment with a 5' complementary sequence to the 3'UTR unique to the target gene. It is of note that compounds such as these are available commercially.

As will be appreciated by one of skill in the art, the miR-200b modulating compound may be delivered intravenously, intra-amniotic, intratracheal or intranasal.

While not wishing to be bound to a particular theory or hypothesis, the inventors note that increasing miR-200b to levels required for normal or compensatory lung development will instruct and regulate downstream target genes, such as genes from the SMAD-driven TGF-β signalling pathway, to promote lung development in order to improve the functional outcome of CDH patients after they are born.

According to a yet further aspect of the invention, there is provided use of a miR-200b modulating compound for treating or preventing abnormal lung development in Congenital Diaphragmatic Hernia (CDH).

As will be appreciated by one of skill in the art, the miR-200b modulating compound may be formulated to be delivered intravenously, intra-amniotic, intratracheal or intranasal.

The lack of success in identifying a genetic cause for CDH led us to investigate the role of epigenetics and more in particular microRNAs. Our study is the first to demonstrate altered miRNA expression in human congenital lung disease. Homogenates of hypoplastic lungs from CDH fetuses display miR-200b and miR-10a overexpression. We then selected tracheal and amniotic fluid samples from fetuses with appropriate or insufficient lung growth following fetal surgery. Responders could be discriminated from non-responders by a significantly higher miR-200 expression in their tracheal fluid, suggesting that stimulated lung development is associated with an increase in miR-200 expression. Upregulation of miR-200b persists in terminal saccules of CDH patients and is associated with decreased TGF-β2 expression. In vitro, miR-200b inhibits TGF-β/SMAD signaling in bronchial epithelial cells.

Using in situ hybridization, we determined that miR-200b is over-expressed in the terminal saccules of postnatal CDH lungs compared to age-matched controls.

The miR-200 family functions by inhibiting several genes involved in the TGF-β/SMAD signaling pathway (26, 33). Increased TGF-β activity enhances miR-200 expression as part of a negative feedback loop (34). Others have previously demonstrated in the surgical sheep model of CDH that FETO increased TGF-β2 expression in hypoplastic lungs (35). In addition, increased TGF-β expression has been observed in hypoplastic lungs in the nitrofen rat model of CDH (36-38).

Here, we observed increased miR-200 expression in prenatal and postnatal lung tissues in CDH and tracheal fluid samples of CDH patients responding to FETO. Our data suggest that the increase in miR-200 might result from an inherent increased TGF-β expression in hypoplastic lungs. In addition, FETO can increase miR-200b expression even further in lungs responding to mechanical stretch via upregulation of TGF-β expression in these lungs.

We established the inhibitory effect of miR-200b on TGF-β/SMAD signaling in human bronchial epithelial cells. Given their epithelial phenotype, these cells displayed a very low level of intrinsic SMAD2/3 activity. miR-200b inhibition significantly enhanced SMAD2/3 phosphorylation, suggesting that in bronchial epithelial cells, miR-200b functions by suppressing endogenous TGF-β activity. Both increased and decreased TGF-β signaling can lead to abnormal lung development (46-48). Our results suggest that miR-200b plays a significant role in normal lung development by closely regulating TGF-β signaling.

Our microarray analysis also revealed upregulation of miR-10a in CDH hypoplastic lungs. Responders to FETO have an increased miR-10a expression, whereas non-responders failed to show a similar response. MicroRNA-10a belongs to the miR-10 family, an evolutionary conserved group of miRNAs located within the HOX gene cluster (49). Thus, upregulation of miR-10a might affect lung growth and development through downregulation of HOX genes. While most miRNAs repress the translation of target messenger RNAs after binding to complementary sequences in the 3' UTR, miR-10a can enhance translation of ribosomal protein messenger RNAs by binding to a 5' terminal oligo-pyrimidine motif (5' TOP). In this way, miR-10a can increase global protein biogenesis. miR-10a is unique that it has been linked to retinoic acid (RA) signaling in a study examining smooth muscle cell differentiation (52). Direct links between retinoic acid, pulmonary development and CDH have been postulated for over 50 years (53-55). Recently, Beurskens, et al., demonstrated lower levels of retinol and retinol binding protein in a large series of cord blood samples from babies with CDH, but not their mothers (56).

Extracellular microRNAs have recently emerged as potential biomarkers since they have been shown to be associated with various pathological conditions including cancer. Biomarkers have also successfully been used to stratify therapy and/or to evaluate response to therapy. Both miR-200 and miR-10a have earlier served as biomarkers in some conditions. Most of these studies have focused on their role in cancer progression. Increased serum miR-200c expression is associated with colorectal cancer progression and metastasis (57) and gastric cancer (58). In contrast, decreased miR-200a expression is associated with poor prognosis and recurrence in ovarian cancer (59). The role of miR-10a as a biomarker is less well established. A recent study showed overexpression of miR-10a in human pancreatic cancer cells (60). Furthermore, a combination of miR-10a and miR-200b has recently been reported to be a valuable microRNA signature for metastatic medullary thyroid carcinoma (61) and bladder cancer (62). We have shown that tracheal fluid expression of miR-200 and miR-10a can serve as a marker of response to FETO. While FETO decreased amniotic miRNA expression, survivors could be distinguished by higher expression of miR-200a, miR-200c, miR-141 and miR-10a.

The first experiment was carefully planned to include only prenatal lungs for identification of potential microRNAs as etiological factors of pulmonary hypoplasia in CDH. CDH is typically diagnosed at second trimester ultrasound (63) and therefore, our three pairs of prenatal CDH and control lungs (22-25 weeks of gestation) form a unique homogenous set of severely hypoplastic lungs, which were not exposed to confounding pre- or postnatal factors directly interfering with lung development (steroids, ventilation, etc.). These lungs were obtained from terminations of pregnancies for medical reasons and processed for research purposes within one hour of termination. In addition, the tracheal and amniotic fluid samples were carefully collected as part of a systematic collection of biofluids in a very well characterized homogenous group of patients undergoing FETO.

We are the first to report altered microRNA expression in clinical cases with abnormal lung development due to severe isolated CDH. Future studies should reveal that manipulating miR-200 and miR-10a expression improves the natural course in CDH patients and their abnormal lung development.

This is the first report demonstrating the potential role of microRNA as an epigenetic factor in pulmonary hypoplasia associated with human CDH and in the nitrofen rat model. Our present study also provides an understanding of how expression of miRNA-200b regulates nitrofen-induced CDH. We have shown for the first time that microRNA-200b contributes in both normal lung development and in CDH. We performed qPCR and ISH to assess the temporal and spatial expression of miR-200b during lung development.

Although in nitrofen lung both PCR and ISH demonstrated lower expression of miR-200b in early stages of lung development, this difference was not significant in PCR. We attribute this difference due to differential expression of miR-200b during lung development. We only consider the difference between nitrofen and control regardless of the level of hypoplasia. This also suggests that miRNA-200b might be a marker of nitrofen effect in this model, rather than hypoplasia. According to our explant and in vivo study, there is a positive relationship between lung branching and miR-200b, therefore we propose that this variation in expression of miR-200b between different embryos is due to the difference in their levels of lung hypoplasia. It is also possible that the observed changes in miRNAs in different embryos might be due to secondary effects of the pulmonary hypoplasia. When we consider herniation and lung hypoplasia in E21, lungs without herniation, second hit in CDH (8) have higher expression of miR-200b than lungs with herniation. This data is consistent with our findings in human CDH lungs, which showed higher expression of miR-200b in trachea fluid of survival baby with CDH.

In Situ Hybridization (ISH) on normal rat lung sections during the pseudoglandular stage of lung development indicate the highest expression in distal cells of the elongating bronchial tree. Rawlins et al. have shown that these distal tip cells are epithelial progenitors that give rise to the more differentiated proximal cells (80). Our ISH showed that nitrofen-induced hypoplastic lungs have fewer numbers of buds with lower expression of miR-200b. According to our ex vivo and in vivo studies miR-200b increased epithelial perimeter and number of buds. All these data indicate the pivotal role of miR-200b in distal tip structure. Recently, Wang et al. have shown that miR-200/ZEB2 pathway can induce pluripotent stem cell generation (81). It suggests that miR-200b may be involved in maintaining the pluripotent feature of distal tip. In mesenchymal cells, the expression pattern of miR-200b is parallel to cellular differentiation. MiR-200b expression in these cells decreases during lung development with increasing differentiation. Distal parabronchial cells are strongly positive for miR-200b, while proximal parabronchial cells are negative. In nitrofen-induced hypoplastic lungs, expression of miR-200b in these distal parabronchial cells is diminished. By using combined ISH/IHC we demonstrate that these miR-200b deficient cells are lipofibroblast transdifferentiated into Alpha-SMA expressing cells (myofibroblast or smooth muscle). This suggests that nitrofen accelerates mesenchymal differentiation into myofibroblast or smooth muscle, associated with decreased expression of miR-200b. It has been shown that lipofibroblasts and ADRP (adipose differentiation-related protein) have a critical role in surfactant synthesis (83). Surfactant deficiency is observed in both human and rat CDH (84, 85). Therefore the role of miR-200b in surfactant synthesis needs to be investigated.

At the cellular level, we indicated the inhibitory effects of nitrofen on expression of miR-200b using human bronchial epithelial (BEAS-2B) cells. Smad-2/3 (TGF-β) signaling is the main cascade in promoting ZEB1 and ZEB2, two well-known targets of miR-200b (86). Previous studies have reported that miR-200 family members repress ZEB1 and ZEB2 genes through epithelial-mesenchymal transition (EMT) process (29, 93). Using luciferase assay and western blotting, we revealed that miR-200b has inhibitory effects on smad2/3 at two main levels: smad2 phosphorylation and ZEB2 expression. Interestingly, nitrofen has the same effects and these effects can be diminished by re-introducing miR-200b. This suggests that nitrofen can promote smad2/3 signaling by decreasing miR-200b expression.

To further understand the effects of miR-200b in the nitrofen-induced CDH model, we addressed the effects of miR-200b on lung explant cultures. Our ex vivo experiments on lung explant cultures indicated that inhibition of miR-200b decreases lung branching buds and perimeter. Re-introducing miR-200b in nitrofen-induced hypoplastic lungs improved the effect of nitrofen on lung branching. This finding suggests that miR-200b regulates the development of hypoplastic lungs in the nitrofen rat model.

Finally, deleting miR-200b in knockout mice results in less compliant lungs due to reduced distal airway branching and thicker alveolar walls with decreased surfactant. This recapitulates the abnormal lung development observed in CDH after birth and suggests that miR-200b is involved in the pathogenesis of adult lung fibrosis.

The invention will now be further described by way of examples; however, the invention is not necessarily limited by the examples.

EXAMPLES

MiR-200b and miR-10a expression are Increased in Fetal Hypoplastic CDH Lungs.

Two miRNAs, miR-200b and miR-10a, were more abundant in prenatal abnormally developed CDH lungs compared to normal control lungs from patients with the same age (P<0.01) (FIG. 1A). We used RT-qPCR to validate the results of the microarray. Both miR-200b and miR-10a had an approximately three-fold greater expression in CDH lungs compared to age-matched control lungs (FIG. 1B). Four other miRNAs: miR-27a, miR-195, let-7a and miR-1—were tested based on near significant differences in the microarray analysis. None of these had a statistically significant difference in expression in CDH lungs compared to control lungs using RT-ciPCR.

Figure 2:
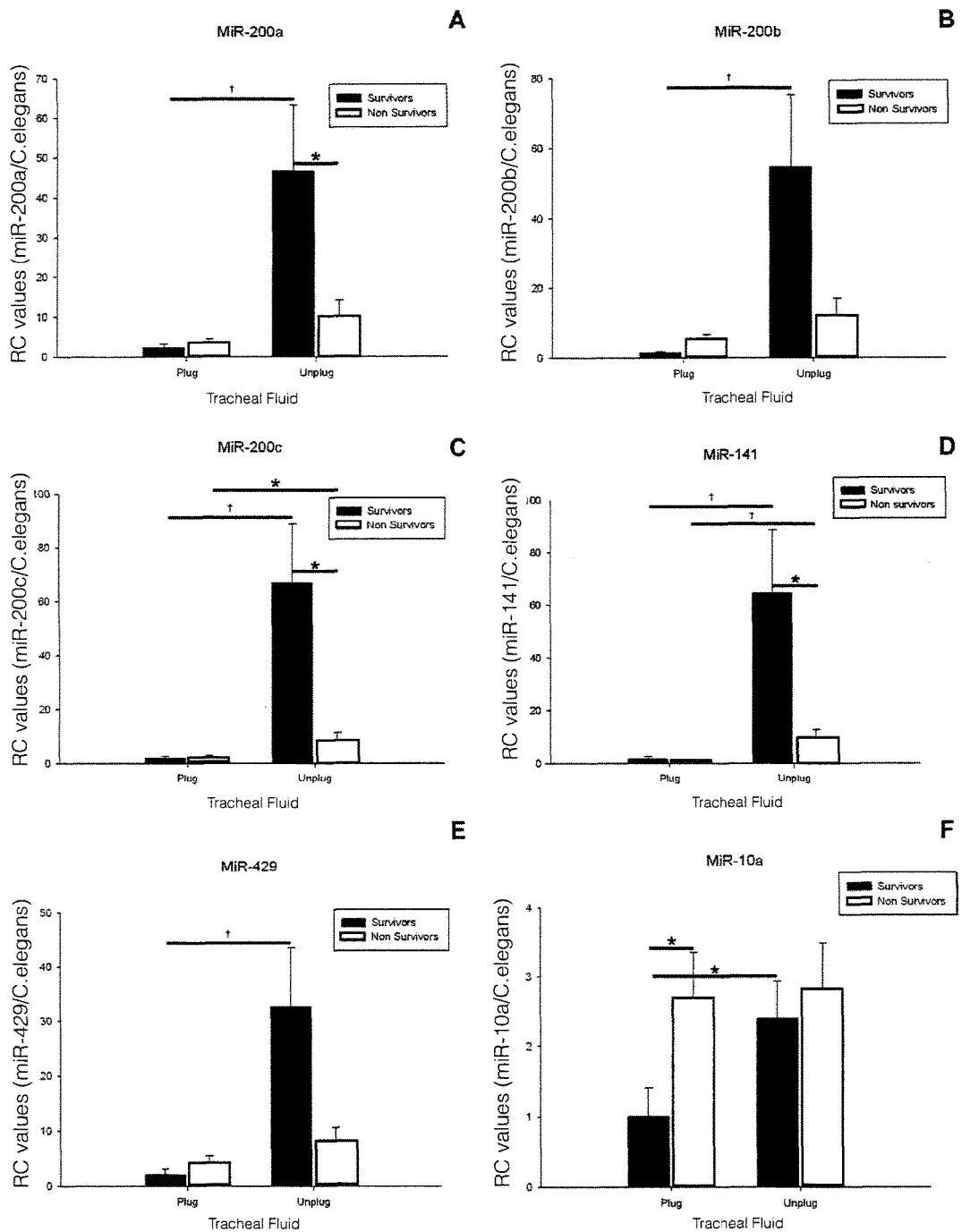
FIG. 2. miR-200 family members and miR-10a expression analysis in tracheal fluid samples of surviving and non-surviving patients with CDH undergoing FETO. Expression levels of miR-200a (A), miR-200b (B), miR-200c (C), miR-141 (D), miR-429 (E), and miR-10a (F) in tracheal fluid samples. Expression levels of these microRNAs were normalized to cel-miR-39. Statistical analysis was performed using the Mann-Whitney U-test for independent comparisons between surviving and non-surviving patients and a Wilcoxon signed-rank test for paired comparisons between plug and unplug, *P<0.05; **P<0.01; *P<0.001.

Tracheal fluid: Responders Have Higher Expression of miR-200 than Non-Responders After FETO Based on these observations, we focused on validating and further exploring the expression of the miR-200 family (miR-200a, miR-200b, miR-200c, miR-141, and miR-429) and miR-10a in tracheal and amniotic fluid samples of CDH patients at baseline (plug) as well as following forced lung growth by FETO (unplug). Responders (i.e. with measurable lung growth and eventually surviving) to FETO had increased expression of the miR-200 family in their tracheal fluid. Expression of miR-200 was considerably higher after FETO (unplug) in responders compared to non-responders (FIG. 2A-E). However, their baseline expression was not different. Conversely, tracheal fluid miR-10a expression was significantly lower in responders compared to non-responders at baseline (plug). Following FETO (unplug), the expression of miR-10a increased significantly in responders, but remained unchanged in non-responders (FIG. 2F). These results indicate that the observed differences in microRNA expression can serve as a biomarker to distinguish survivors from non-survivors after FETO for abnormal lung development in CDH.

Expression of miR-200 Family and miR-10a in Amniotic Fluid Increases After FETO.

Figure 3:
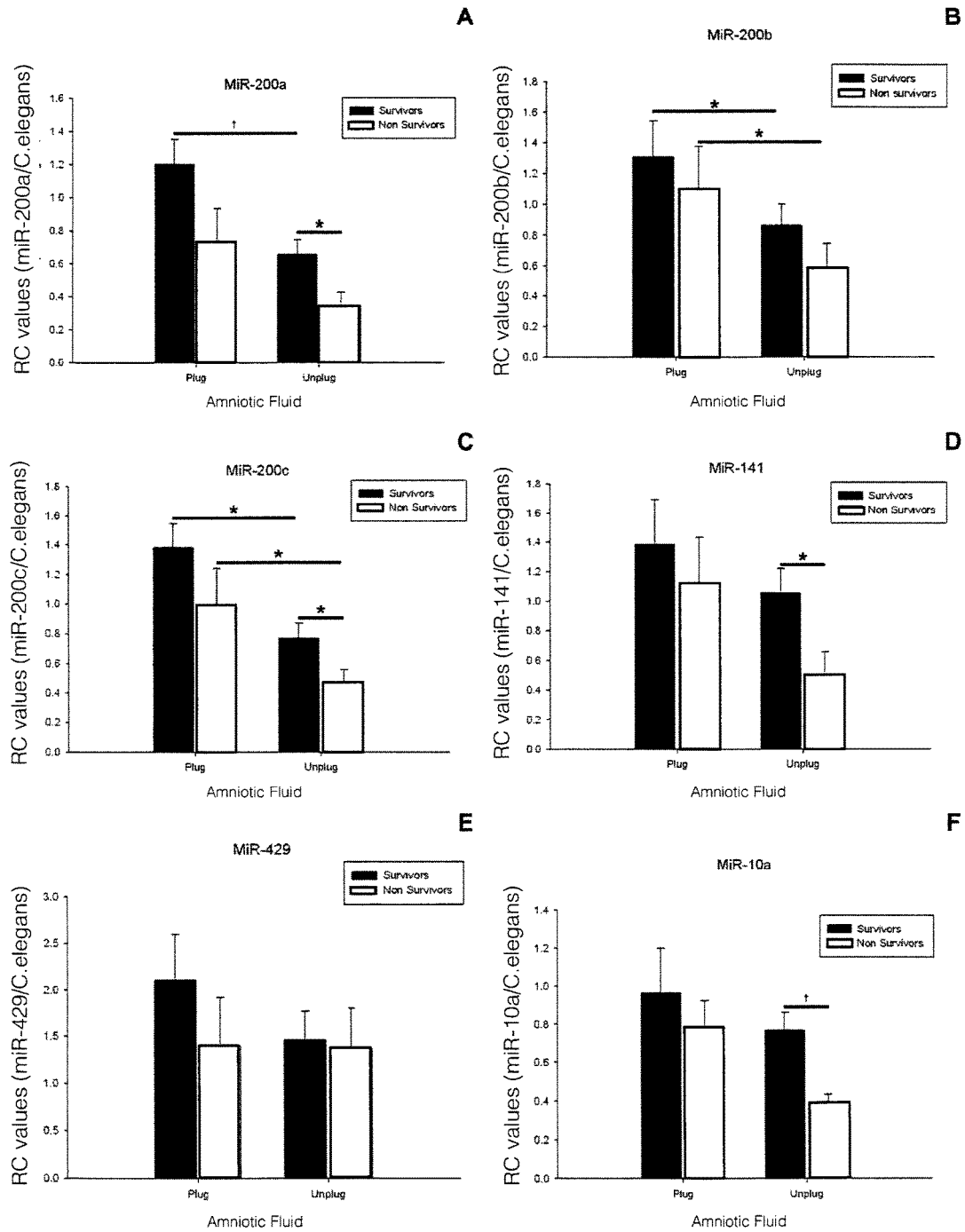
FIG. 3. miR-200 family members and miR-10a expression analysis in amniotic fluid samples of surviving and non-surviving patients with CDH undergoing FETO. Amniotic fluid levels of miR-200a (A), miR-200b (B), miR-200c (C), miR-141 (D), miR-429 (E), and miR-10a (F). Expression levels of these microRNAs were normalized to cel-miR-39. Statistical analysis was performed using the Mann-Whitney U-test for independent comparisons between surviving and non-surviving patients and a Wilcoxon signed-rank test for paired comparisons between plug and unplug, *P<0.05; **P<0.01.

Following FETO (unplug) the amniotic fluid levels of the investigated miRNAs did not mirror what was observed in the tracheal fluid. The amniotic fluid levels were overall lower. Since the lungs contribute largely to the amniotic content in the third trimester and were occluded during FETO, this was anticipated (25). The expression profiles of all investigated microRNAs exhibited a similar trend: FETO responders had significantly higher expression than non-responders (FIG. 3). More specifically, expression of miR-200a and miR-200c significantly decreased after FETO (unplug) (FIGS. 3A and C). Expression of miR-200a, miR-200c, miR-141 and miR-10a was higher in amniotic fluid of survivors compared to non-survivors after FETO (unplug) (FIGS. 3A, C, D and F).

Expression of miR-200b is Higher in The Distal Part of Postnatal Hypoplastic Lungs.

Figure 4:
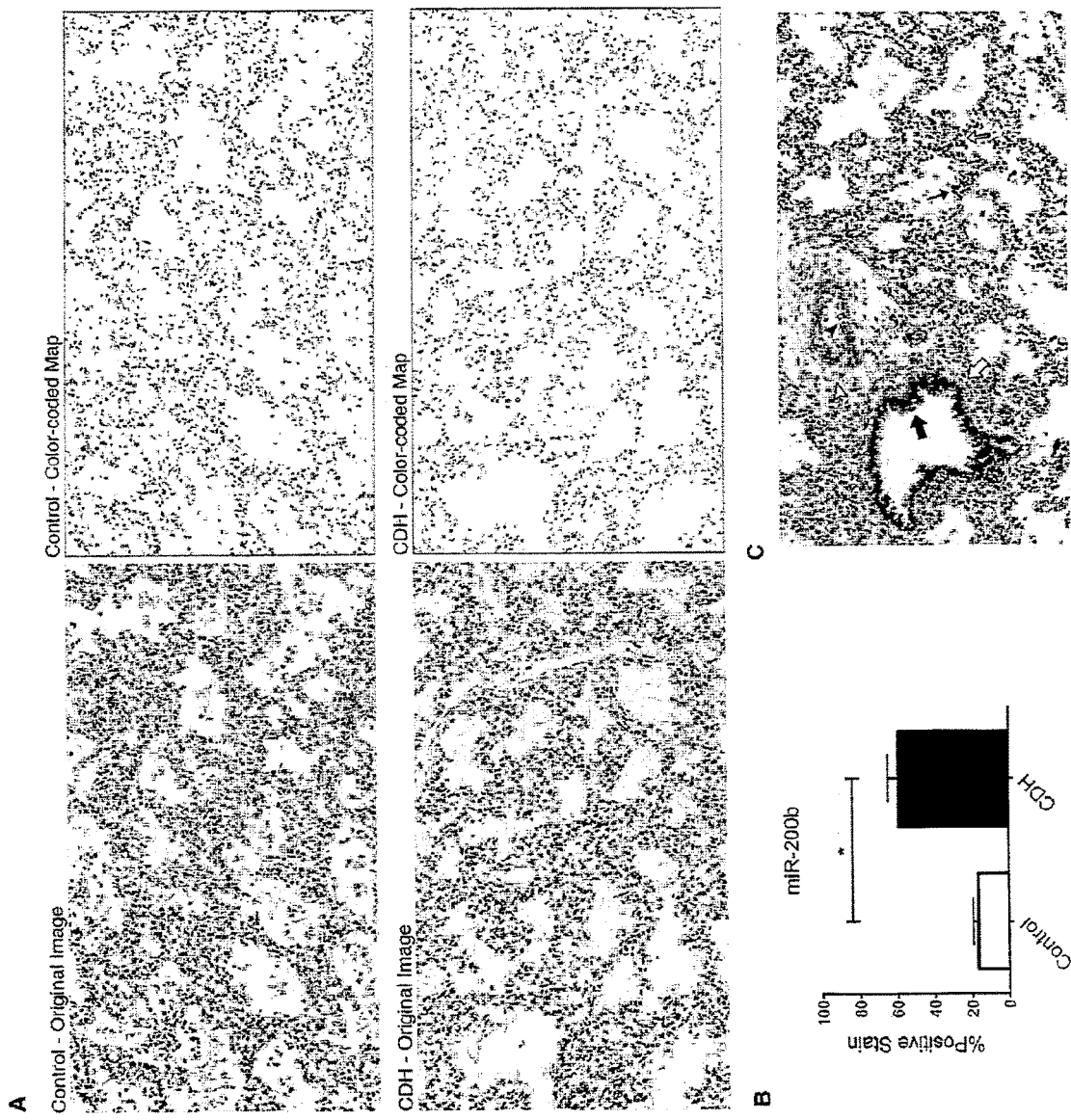
FIG. 4. In situ hybridization for miR-200b (blue stain) in postnatal lung (methyl green counterstain, 200× magnification). (A) Terminal saccules of control vs. CDH lungs (color-coded maps: blue=positive staining, green=negative staining, aqua=colocalized positive and negative staining). (B) Area of positive staining (% blue+% aqua) was calculated for each lung section (*P<0.05). (C) miR-200b expression in normal postnatal lung. In bronchioles, miR-200b is expressed in epithelial cells (black thick arrow), but is absent from parabronchial smooth muscle cells (white thick arrow). In blood vessels, miR-200b is expressed in endothelial cells (black arrowhead), but is absent from the surrounding smooth muscle cells (white arrowhead). Terminal saccules contain a mixed population of miR-200b-positive (black thin arrow) and miR-200b-negative (white thin arrow) cells.

We performed in situ hybridization to determine miR-200b expression in a separate set of postnatal lung sections. Hypoplastic CDH lungs were characterized by increased miR-200b expression, particularly in the terminal saccules and alveoli (FIG. 4A). We used image analysis software to generate color-coded maps and quantify the area of positive staining for each lung section. Using this method, neonatal hypoplastic CDH lungs displayed increased miR-200b expression compared to age-matched control lungs (FIG. 4B).

In Situ Hybridization for miR-200b Produced a Highly Specific Staining Pattern in Normal Neonatal Lungs.

Bronchial epithelial cells were intensely positive for miR-200b (FIG. 4C, thick black arrow). In contrast, parabronchial smooth muscle cells were predominantly negative for miR-200b (FIG. 4C, thick white arrow). Terminal saccules contained a mixed population of positive (alveolar type II cells) and negative-staining cells. In blood vessels, endothelial cells (inner layer) were positive for miR-200b (FIG. 4C, black arrowhead). Perivascular smooth muscle cells, on the other hand, were negative (FIG. 4C, white arrowhead). Mesothelial cells of the pleura were positive for miR-200b.

TGF-β, a miR-200b Target Gene, Expression is Decreased in Hypoplastic CDH Lungs

Figure 5:
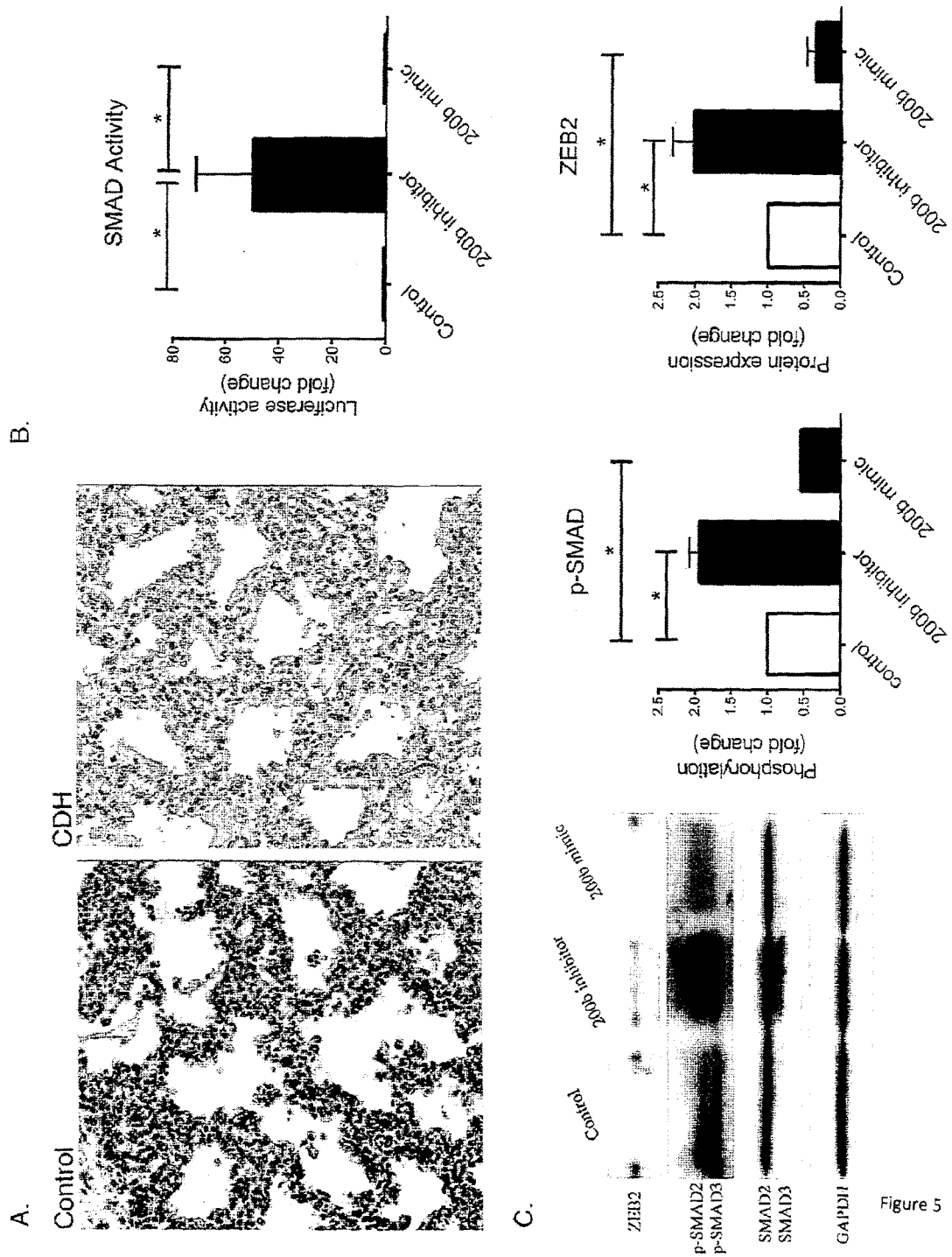
FIG. 5. miR-200b Target Gene Expression. (A) Immunohistochemistry for TGF-β2 (brown stain) in control vs. CDH postnatal lungs (hematoxylin counterstain, 200× magnification). (B) SMAD-luciferase reporter assay in cultures of bronchial epithelial cells. Luciferase activity was measured after a 48-hour incubation with miR-200b inhibitor, mimic or control oligonucleotide. (C) Immunoblotting for ZEB2 and phospho-SMAD (p-SMAD). Bronchial epithelial cells were incubated for 48 hours with miR-200b inhibitor, mimic or control oligonucleotide. (*P<0.05)

Others have identified components of the TGF-β-induced signal transduction pathway as the major targets of the miR-200 family (26). We used immunohistochemistry to assess TGF-β2 expression in postnatal lung tissues. The cellular distribution of TGF-β2 was very similar to miR-200b, i.e. expressed in bronchial epithelial cells and vascular endothelial cells, but absent from parabronchial and perivascular smooth muscle cells. CDH lungs displayed decreased TGF-β2 expression in terminal saccules compared to age-matched control lungs (FIG. 5A).

MiR-200b Down Regulates TGF-β Signaling in Human Bronchial Epithelial Cells

Downstream effects of TGF-β-induced signal transduction are initiated through SMAD2/3 phosphorylation and its subsequent nuclear translocation (27). We used a luciferase bioluminescent assay to measure SMAD-induced gene expression and the impact of changing miR-200b expression in cultures of human bronchial epithelial cells. In a pilot experiment measuring miR-200b expression in different cell lines relevant to lung, we demonstrated that these cells exhibit abundant miR-200b expression. In absence of exogenous TGF-β, bronchial epithelial cells displayed very little SMAD-dependent luciferase activity. This low baseline activity did not change when miR-200b mimics were added to the culture medium. On the other hand, inhibitors of miR-200b increased SMAD-luciferase activity by several orders of magnitude (FIG. 5B). Collectively, these data suggest that basal TGF-β-induced signaling is tempered by steady state levels of miR-200b, and that reducing miR-200b is permissive for TGF-β-induced signaling.

In order to clarify mechanisms that might underpin altered basal SMAD-mediated responses, we next performed Western blotting using antibodies against total SMAD2/3 and phospho-SMAD2/3 (p-SMAD). Addition of miR-200b inhibitors or mimics to cultures of bronchial epithelial cells resulted in a nearly twofold increase or decrease, respectively, in p-SMAD levels; however, total SMAD2/3 abundance was unaffected (FIG. 5C). ZEB2 is a downstream transcriptional repressor in the TGF-β/SMAD signal transduction pathway and a putative target of miR-200b based on sequence complementarity (27). Addition of miR-200b inhibitors or mimics to cultures of bronchial epithelial cells resulted in a nearly twofold increase or decrease, respectively, in ZEB2 levels (FIG. 5C).

MiR-200b Expression is Decreased in Nitrofen Rat Model of CDH.

Figure 6B:
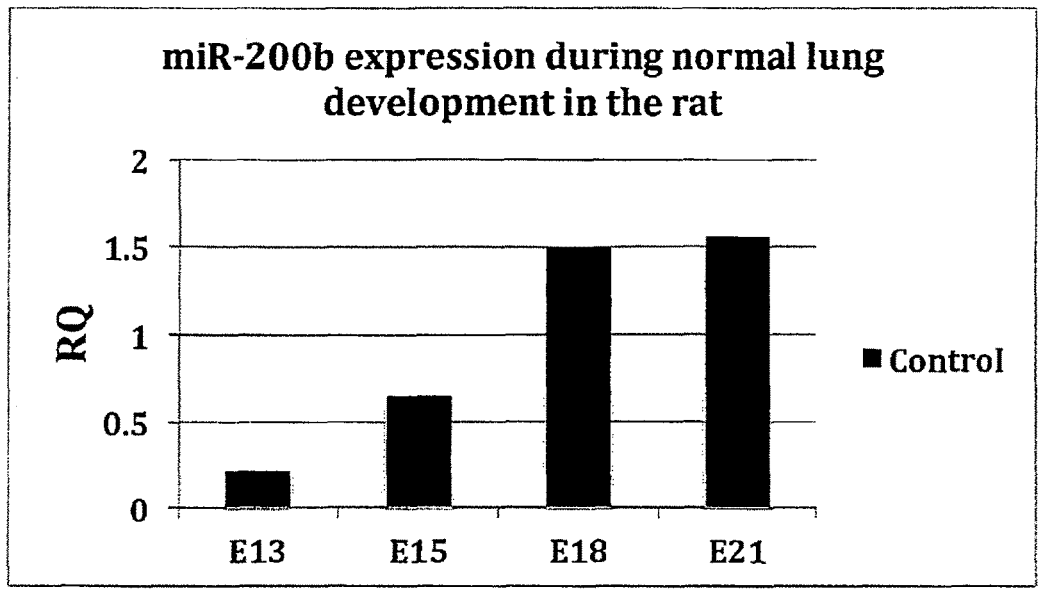
FIG. 6. miR-200b expression during normal lung development and in CDH rat model. (a) Real-time PCR for miR-200b expression on lungs from controls at embryonic day (E) 13, 15, 18 and 21. (b) The expression of miR-200b is dynamic and increasing during normal lung development. miR-200b expression was decreased in nitrofen rat lungs compared to control in E13, 15 and E18 with no difference at E21. (c) In Situ Hybridization (ISH) on normal and nitrofen lungs showed down-regulation of miR-200b in early stages of lung development (200× magnification). Control lung and nitrofen (CDH) lungs. blue=positive staining, green=negative staining). Undifferentiated splanchnic mesenchyme is positive for miR-200b. In control lungs, distal parabronchial cells (arrow) are positive for miR-200b, while proximal parabronchial cells are negative. In nitrofen-treated lungs, both distal and proximal parabronchial cells are negative for miR-200b. (d) In Situ Hybridization (ISH) for miR-200b on serial section of normal rat lung at EIS. miR-200b express both in epithelial and mesenchymal layers. The highest expression is observed on tip structure of branching point (black arrow).
Figure 6B:
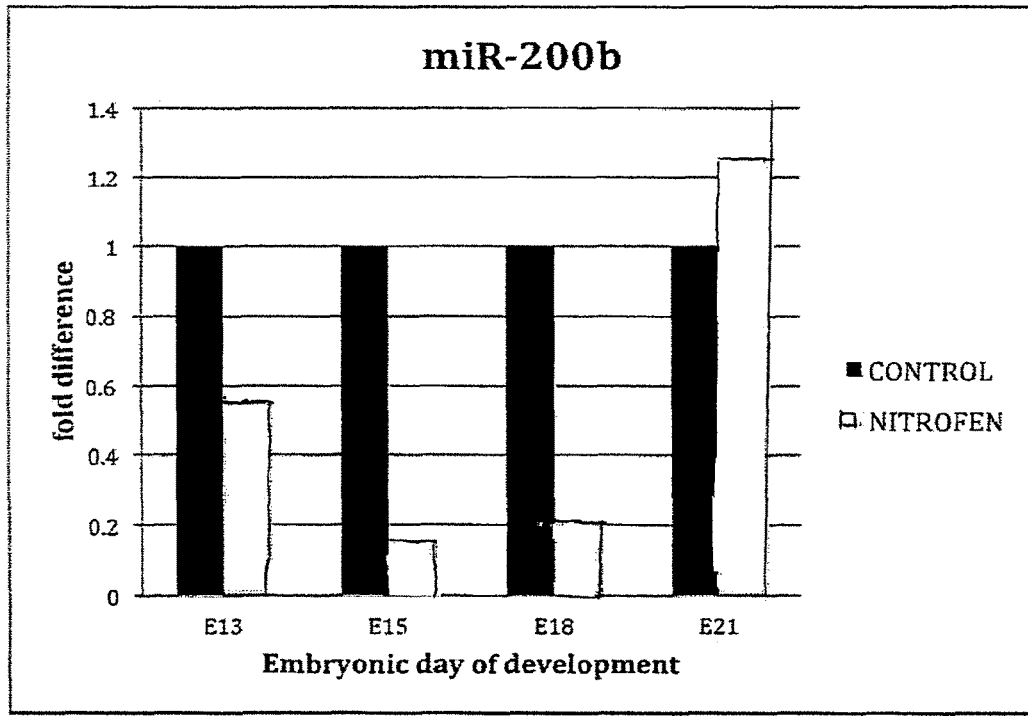
Figure 6C:
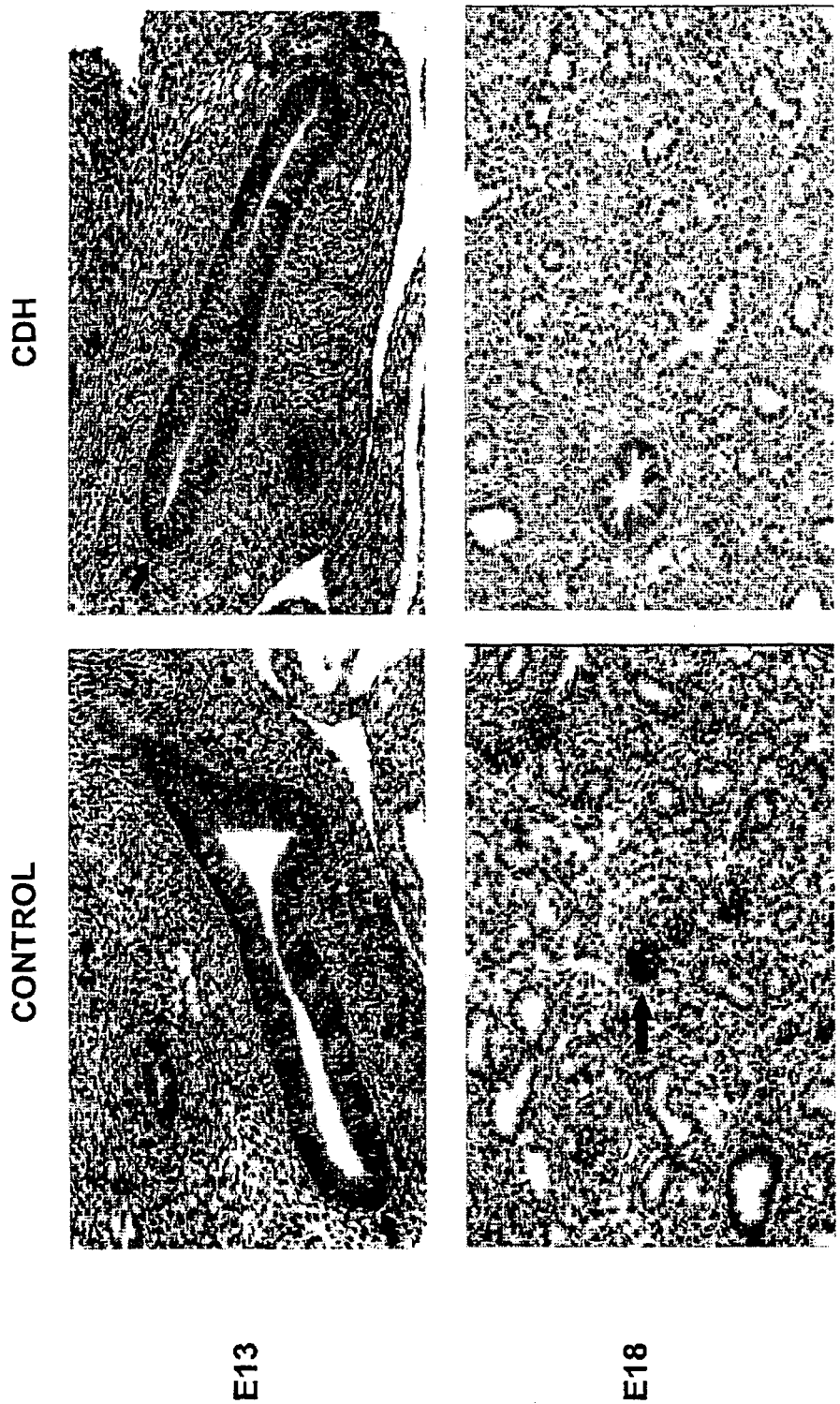
Figure 6D:
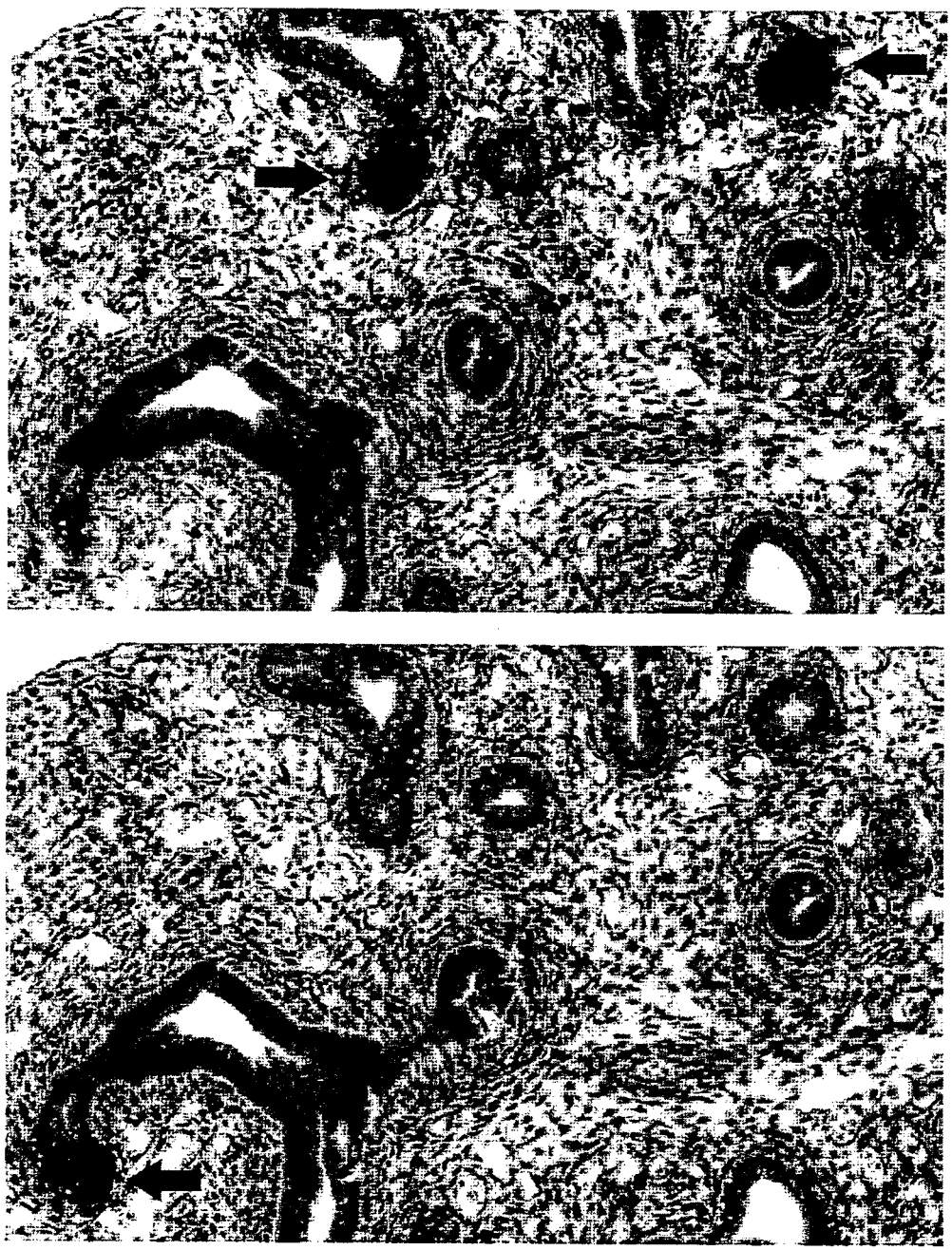

To evaluate the temporal and spatial expression of miR-200b in the nitrofen rat model during lung development, we performed rt-qPCR and in situ hybridization (ISH) on lung tissues at embryonic day (E) 13, 15, 18 and 21. The qPCR results demonstrate that miR-200b expression is dynamic during normal lung development in the rat (FIG. 6A). They also clearly demonstrate that during the early stages of lung development (E13) to the end of pseudoglandular stage (E18) the expression of miR-200b is lower in nitrofen lungs than in the control (FIG. 6B). However the expression of miR-200b at the saccular stage (E21) is higher than the control, similar to what we observed in humans (FIG. 6B, compare to FIG. 1). Next we performed in situ hybridization to evaluate the cellular distribution of miR-200b in rat lung tissues in both normal and CDH rat model. In parabronchial mesenchyme, miR-200b exhibited higher expression towards distal surface and surrounding the elongating tips (FIG. 6c ). In contrast to nitrofen rat model, lungs had lower miR-200b expression that is more prominent in mesenchymal layer, particularly in mesenchyme layer surrounding the distal epithelium at E13 and E15 (FIG. 6C). In the pseudoglandular stage of lung development (E13 and E15), serial sectioning of normal lung revealed the highest expression of miR-200b at the tips of the growing bronchial tree (FIG. 6D). These results establish the spatial and temporal expression of miR-200b in the rat model which allowed us to evaluate miR-200b expression early on in development at stages not accessible in human CDH.

Figure 7A:
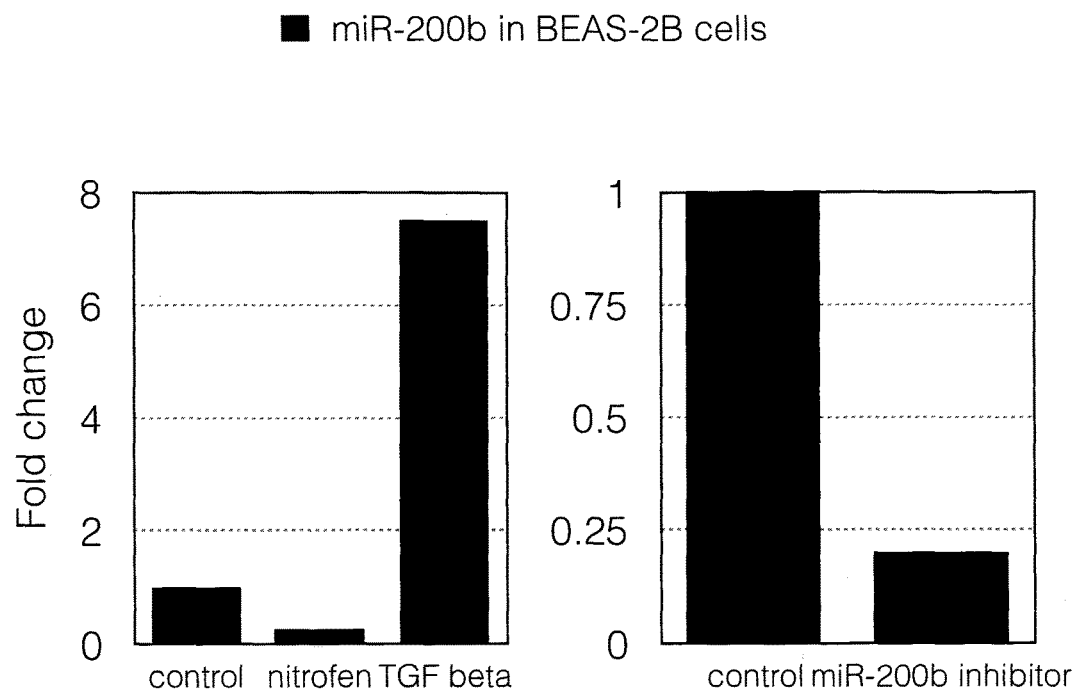
FIG. 7. Role of miR-200b and nitrofen in bronchial epithelial cells. (a) expression of miR-200b decreased in BEAS-2B cell treated with nitrofen than control. (b) Effect of miR-200b and nitrofen on SMAD2/3 signalling as measured by dual luciferase assay. Bronchial epithelial cells transfected with miR-200b inhibitors or nitrofen stimulate smad2/3 signalling. miR-200b mimic (overexpression of miR-200b) decrease the effect of nitrofen on smad2/3 signalling. (c) Inhibition of miR-200b or nitrofen promotes SMAD2 phosphorylation as measured by western blot. In bronchial epithelial cells, miR-200b inhibitors or nitrofen stimulate smad2 phosphorylation and miR-200b mimic (overexpression of miR-200b) decrease the effect of nitrofen on smad2 phosphorylation. (c) Inhibition of miR-200b or nitrofen can promote ZEB2 expression and over expression of miR-200b can reduce it. *P-values are <0.05. Data represent the mean of three independent experiments.

MiR-200b Expression is Decreased in Nitrofen Treated Human Bronchial Epithelial Cell To explore the effects of nitrofen on the expression of miR-200b at the cellular level, we used human bronchial epithelial cell, (BEAS-2B) and measured the expression of miR-200b in treated with nitrofen after 48 h. The result demonstrates significantly lower expression of miR-200b in nitrofen treated cells than untreated ones (FIG. 7A). This confirms in vitro that nitrofen decreases miR-200b expression in bronchial epithelial cells.

MiR-200b Diminishes Nitrofen-Induced SMAD2/3 Signaling

Figure 7B:
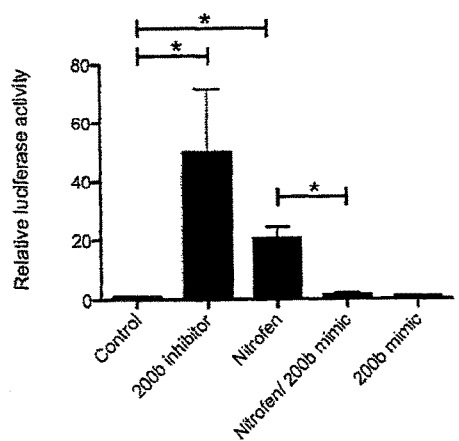

To determine the potential impact of miR-200b and nitrofen on smad2/3 signalling and EMT markers, we performed a dual luciferase assay and Western blotting on human bronchial epithelial cells. In the absence of exogenous TGF-β, bronchial epithelial cells displayed decreased SMAD-luciferase activity. Transfecting the cells with miR-200b inhibitor or treatment with nitrofen increased SMAD-luciferase activity by several orders of magnitude. Increased SMAD signaling due to nitrofen treatment declined to the basal level when cells were transfected with miR-200b mimic (FIG. 7B).

Figure 7C:
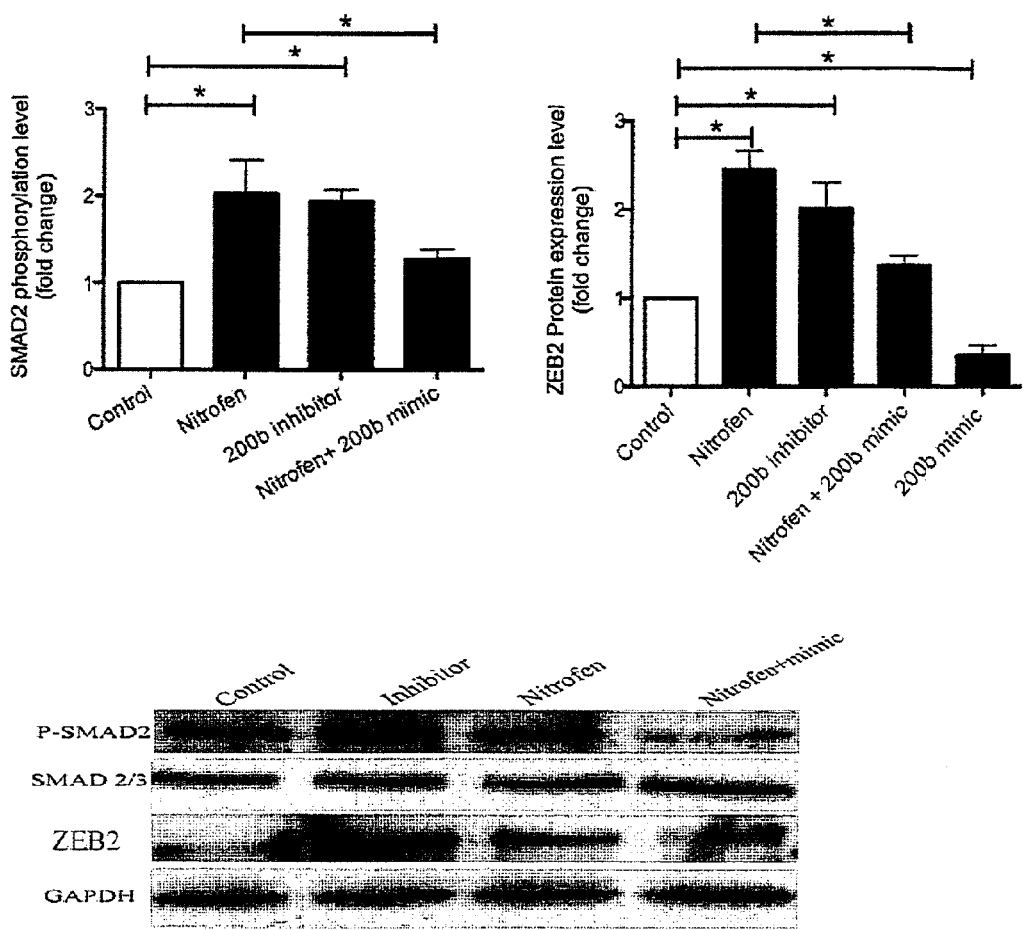
Figure 8A:
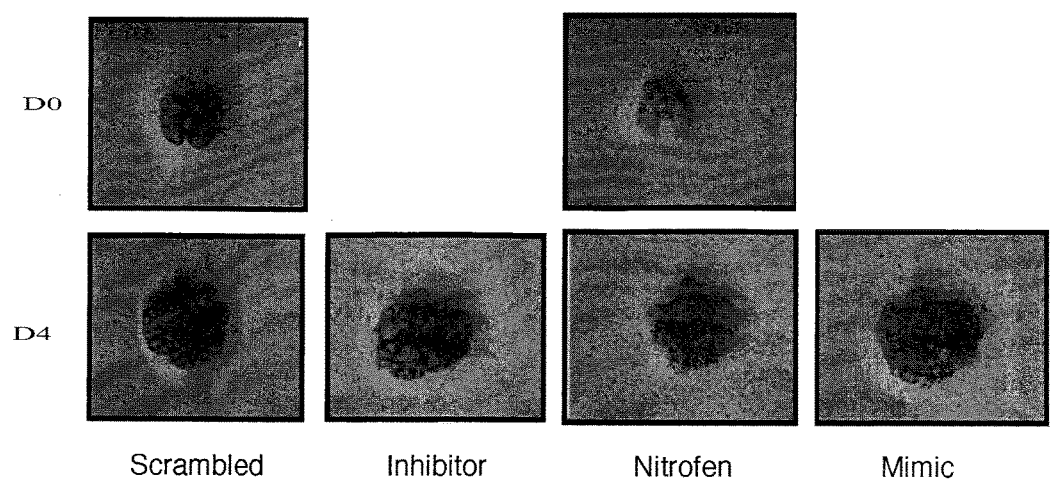
FIG. 8A: miR-200b and lung branching morphogenesis. E13 control (A) and nitrofen (D) lungs were cultured for 4 days as described and treated with 200 nM scrambled negative control (B,E), 200 nM miR-200b antagomirs (C) or 200nM miR-200b mimics (F). miR-200b knock-down caused reduced branching (C) and reduced branching due to nitrofen was abrogated by miR-200b mimics (F).
Figure 8B:
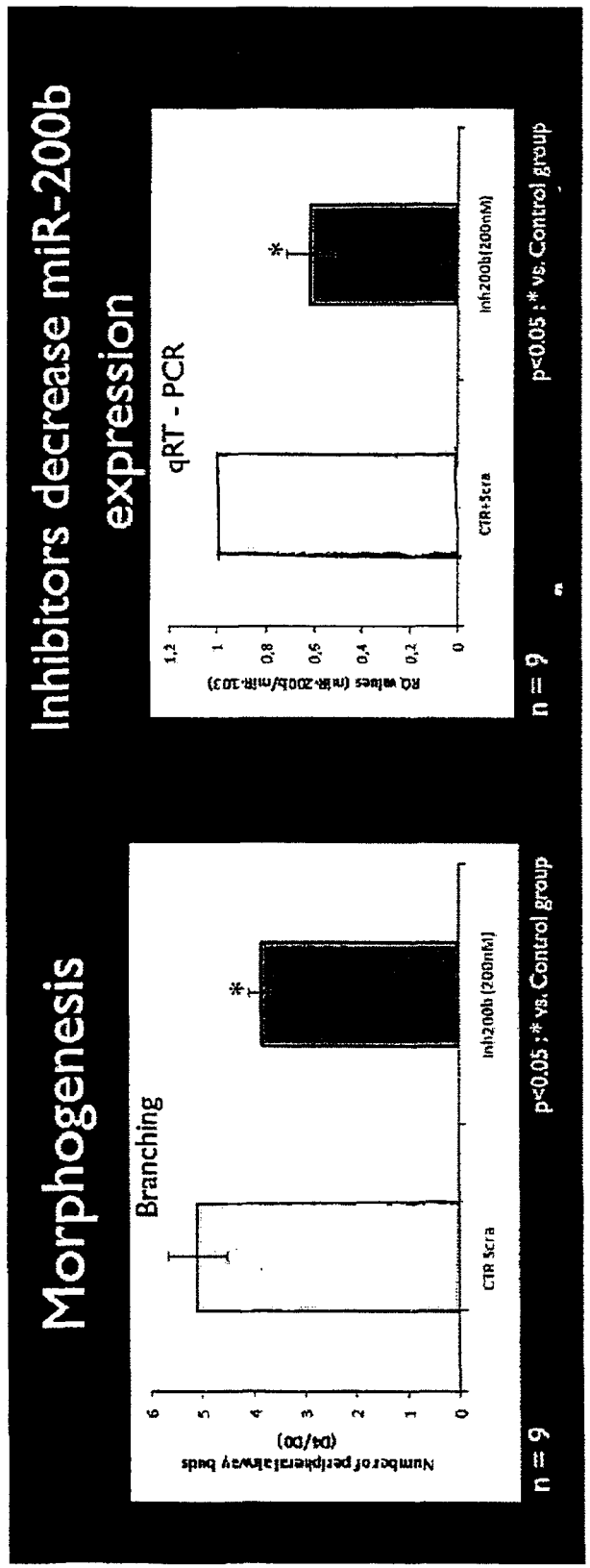
FIG. 8B Branching morphogenesis is significantly reduced in E13lung explants treated with 200 nM miR-200b inhibitors (left). We confirmed with qRT-PCR that treatment with 200 nM miR-200b inhibitors significantly reduced miR-200b expression in the treated lung explants (right).
Figure 8C:
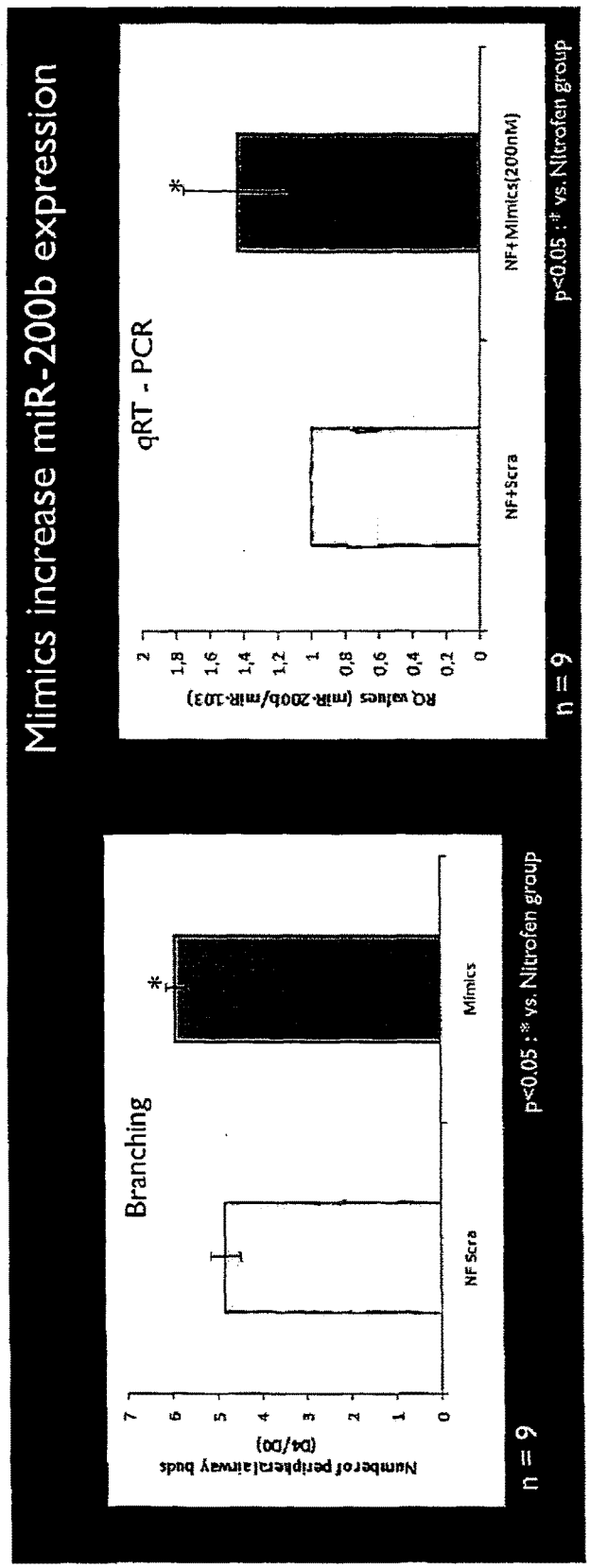
FIG. 8C: Branching morphogenesis significantly improves in E13 nitrofen-induced hypoplastic lung explants treated with 200 nM miR-200b mimics (left). We confirmed with qRT-PCR that treatment with 200 nM miR-200b mimics significantly increases miR-200b expression in the treated nitrofen-induced hypoplastic lung explants (right)

Next we performed western blotting for SMAD2 and phospho-SMAD2 to confirm luciferase result and determine whether protein expression or phosphorylation could impact the alteration of SMAD signaling. P-SMAD protein concentration in miR-200b transfected or nitrofen treated BEAS-2B cells significantly increased when compared to untreated cells. Nitrofen treated cells transfected with miR-200b mimic had significantly lower p-SMAD2 than nitrofen treated or untreated cells. However, total SMAD2 concentration remained unaffected (FIG. 7C). Inhibition of miR-200b or nitrofen promotes ZEB2 (FIG. 7C) but not TGF-β2 expression. ZEB1 expression was not affected by inhibition of miR-200b or nitrofen, but its expression slightly decreased by the overexpression of miR-200b. These results indicate that the nitrofen-induced decrease in miR-200b expression leads to increased target gene expression (SMAD-driven TGF-β signalling) that can be "treated" by normalizing miR-200b expression in the BEAS-2B cells.
Role of miR-200b in Fetal Lung Development:

To identify the effect of alterations of miR-200b in lung development, we cultured lung explants (n=36) at E13 in four experimental groups for 96 hours (9 for each group from 3 different litters). In order to evaluate the role of miR-200b during lung morphogenesis ex vivo, after harvesting, we treated normal lung explants with miR-200b inhibitors (200 nM), or miR-200b scramble (oligo negative control). Similarly, nitrofen exposed embryos were also treated with miR-200b (200 nM) or oligo negative control. The miR-200b inhibitor affects lung branching causing a significant decrease in total number of peripheral airway buds (FIG. 8A, B) and epithelial perimeter (FIG. 8A, B) of lung explants. In contrast, normalizing miR-200b expression with mimics abrogates the nitrofen effects on lung branching with an increase in peripheral airway buds (FIG. 8A, B) and epithelial perimeter (FIG. 8A, B). We confirmed the expression levels of miR-200b by RT-qPCR to ensure transfection efficiency in lung explant cultures (FIG. 8C). These results confirm that normalizing miR-200b expression improves nitrofen-induced abnormal lung development in vitro.

MiR-200b Mimic Treatment Improves Fetal Lung Growth

Figures 1, 9B:
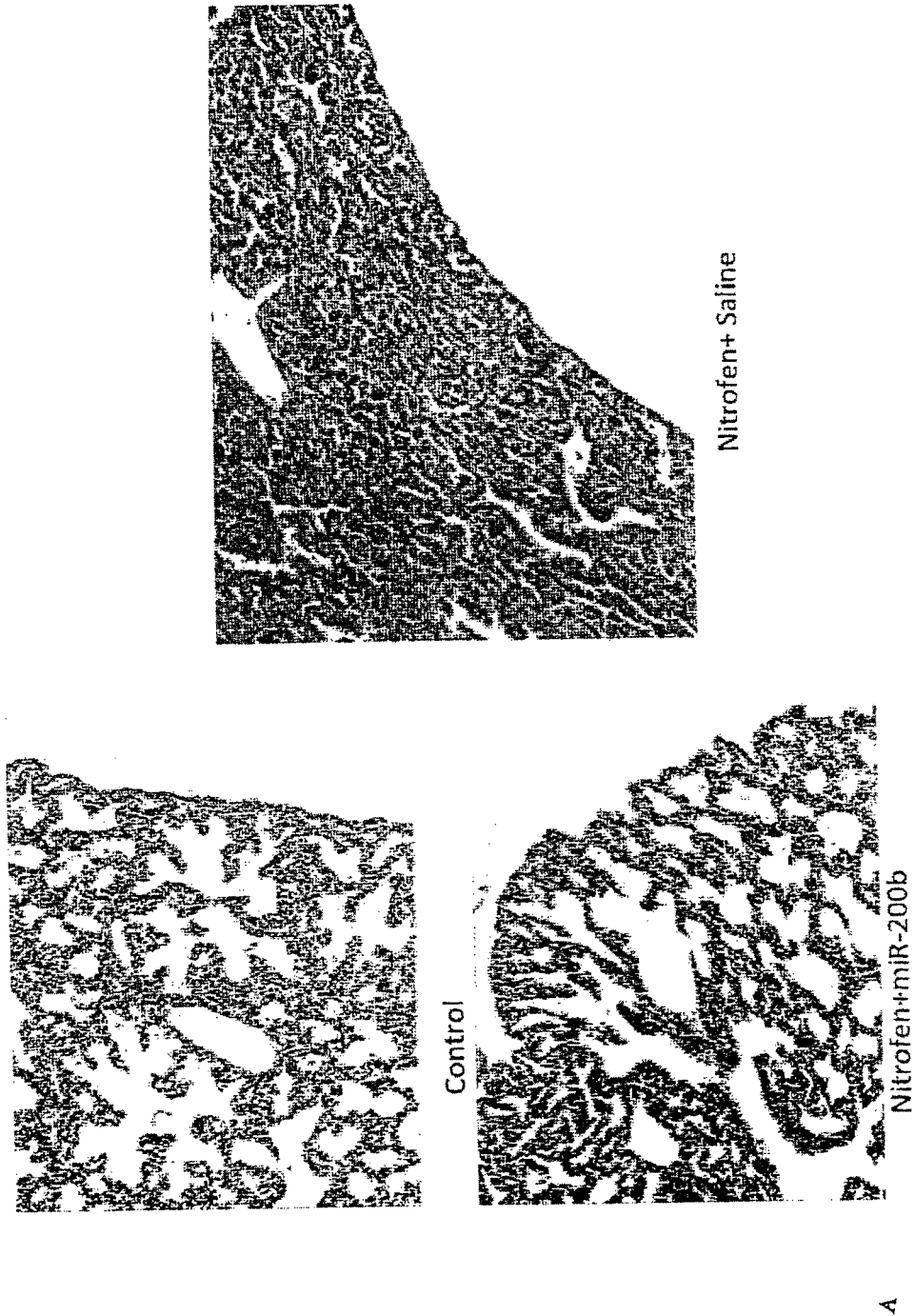
FIG. 9B: Preliminary histological (A) and morphometric analysis (B) of nitrofen-induced hypoplastic lungs that we treated with 5 mg/kg miR-200b mimics in utero via transplacental administration. The dramatic histological improvement (A) was statistically significant in a morphometric analysis in which we determined the radial alveolar count (B)

To further investigate the effects of miR-200b mimic treatment, we treated pregnant dams with 5 mg/kg miR-200b mimics via tail vein injection right after nitrofen administration. First, we saw a reduction in diaphragmatic defect incidence from 70% to 10% in the offspring of rats treated with miR-200b mimics. In addition, we observed significantly improved total lung growth in nitrofen-induced abnormal lungs compared to nitrofen lungs with no treatment (saline). LW/BW was significantly higher in mimic treated lungs relative to untreated ones, resulting in better oxygenation and improved survival (FIG. 9A). Treatment with miR-200b mimic partially recovers lung hypoplasia in promoting normal lung growth (FIG. 9B).

Morphometric Studies

Figures 2, 9B:
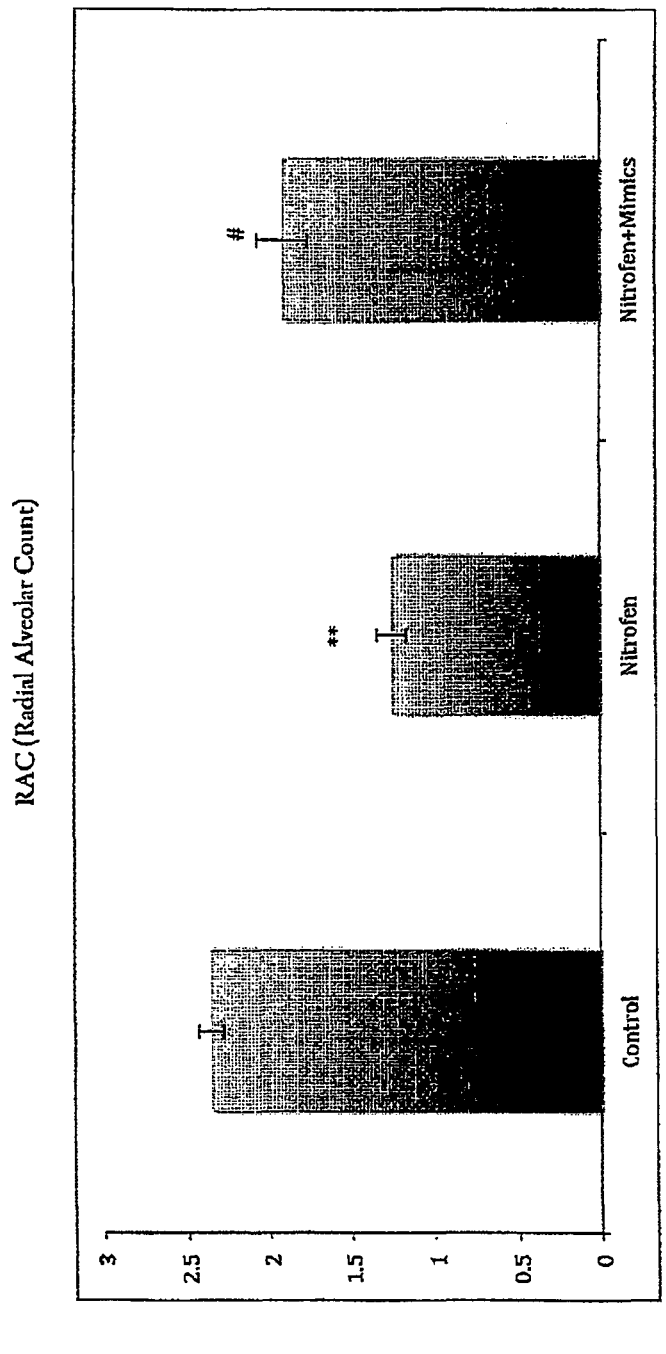

H&E staining showed that after miR-200b mimic treatment of normal lungs, a pattern of decreased alveoli development was observed. However, in CDH lungs treated with miR-200b mimics, the effect on alveoli was nullified (FIG. 9). Considering Radial Saccular Count (RSC), the histological analysis of lung architecture showed that CDH lungs after treatment with saline (CDH+S) demonstrated thicker septal and saccular walls and an increased amount of interstitial tissue compared to control lungs. However CDH lungs treated with mimics (CDH-FM) showed remarkable development of the saccules and airspaces compared to non-treated lungs (FIG. 9B). Further RSC analysis revealed that RSC values were significantly increased when compared to non-treated lungs in miR-200b treated lungs (FIG. 9B). Lastly, we assessed the medial arteries thickness and observed an increase in all the diameters analysed in the CDH-ES group compared to control lungs and miR-200b mimic treated lungs, with no statistically significant differences. Similarly, we also observed that the arteries look similar in all the groups.

Microrna Screen of Lung Specimens

RNA Isolation

ErasmusMC-Sophia's institutional review board approved the study protocol and all the experiments were performed adhering to the relevant guidelines of the Research Ethics Board of the University of Manitoba. Surrogates provided consent for the use of human tissues and biofluids. We biopsied lungs from three fetuses with isolated and severe CDH and three age-matched controls without lung disease (22, 22 and 25 weeks of gestation) undergoing termination or pregnancy. Total RNA of these lung specimens was extracted using Trizol reagent (Invitrogen Life Technologies, Carlsbad, Calif., USA).

MicroRNA Profiling

The expression profile of 319 human miRNAs was investigated using a liquid-phase bead-based array. In brief, 5 µg of total RNA was biotinylated at the 3' end using the FlexmiR MicroRNA labeling kit (Luminex, Austin, Tex., USA), according to the manufacturer's instructions. The labeled RNA was hybridized to locked nucleic acid (LNA) capture probes. Each probe is bound to a fluorescently dyed xMAP bead. Following washes, the biotinylated miRNAs were detected by reaction with streptavidin-phycoerythrin (SAPE). The samples were analyzed on a Luminex-200 instrument capable of identifying the fluorescent bead and measuring SAPE intensity. The measured intensities were subtracted from a background control reaction and normalized against a set of ubiquitously expressed small nucleolar RNAs (snoRNA). Heat maps and statistical analyses were generated using the Institute for Genomic Research Multi Experiment Viewer.

Real-Time Polymerase Chain Reaction (RT-qPCR)

We used the miRCURY LNA PCR system according to the manufacturer's instructions (Exiqon, Vedbaek, Denmark). Locked nucleic acid (LNA) primer sets were purchased from Exiqon (Table 1). Following reverse transcribing of the isolated RNAs, we used the SYBR Green assay (Bio-Rad, Hercules, Calif., USA) for qPCR amplification. We included three small RNA species as endogenous controls (SNORD38B, 5S rRNA and U6 snRNA). Of these, SNORD38B had the most stable expression between different samples and was used to normalize the data.

Biomarker Screen of Biofluids (Amniotic and Tracheal Fluids)

Clinical Evaluation

Ultrasound evaluation was performed <48 hrs before FETO plug (further referred to as baseline, typically around 26-28 weeks) and <48 hrs before balloon removal (typically around 34 weeks). The degree of pulmonary hypoplasia was estimated using 2D ultrasound and was expressed as a lung-to-head ratio (LHR) (13, 14). The area of right lung was measured in a transverse plane of the fetal chest at the level of the 4-chamber view. The borders of the right lung were manually traced. The head circumference (HC) was measured in a standard transverse section of the fetal brain displaying the midline dividing the two hemispheres, the posterior horns of the lateral ventricles and the cavum septi pellucidi. The LHR is corrected for gestational age by expressing the LHR of the index case as a proportion of what is normally expected for a gestational age matched normal fetus (observed/expected: O/E LHR). The relative increase in O/E LHR compared to the baseline value was expressed as follows: ((O/E LHR unplug−O/E baseline)/O/E baseline)×100%.

The functional status of the pulmonary circulation was evaluated using a maternal hyperoxygenation test (15). This test was performed when the fetus was positioned with the right lung proximal to the probe, allowing accurate identification of the pulmonary vessels. In the first branch of the pulmonary artery after its entry in the lung a pulsed-wave Doppler flow waveform was recorded. Three separate Doppler measurements were expressed as pulsatility index (PI) and averaged. Subsequently, this was repeated during continuous maternal hyperoxygenation using inhalation of a mixture of room air and 100% oxygen (9 L/min via a face mask) for at least 10 min. The relative difference between pre- and posthyperoxygenation values was expressed as deltaPI: ((baseline PI-PIO2)/baseline PI)×100% (15, 16).

RNA Isolation

Amniotic and tracheal fluid were collected at the time of balloon insertion (further referred to as baseline, typically around 26-28 weeks) and its removal (typically around 34 weeks) (n=21). Amniotic fluid was retrieved at first entry into the amniotic cavity; tracheal fluid was sampled below the vocal cords, through the fetoscopic sheath, taking care not to contaminate it by irrigation fluid. The Ethics Committee of the UZ Leuven has approved the fetal treatment and prospective follow-up program of patients with CDH, as well as the use of fetal fluid specimens to improve prenatal prediction of outcomes. We selected archived (−80° C.) sample pairs from 11 consecutive "responders" (defined as having a marked increase in 0/ E LHR from baseline and who eventually survived) and 10 non-responders (i.e. poor or absent increase in lung size and eventual neonatal death (17)) (Table 2). The relative increase in O/E LHR compared to the baseline value was expressed as follows: ((O/E LHR unplug−O/E baseline)/O/E baseline)×100%. Blinded to clinical outcome, total RNA was extracted for RT-qPCR using the miRCURY™ RNA Isolation Kit for Biofluids (Exiqon). Briefly, 220µL of amniotic fluid and tracheal fluid from each time point were thawed on ice and centrifuged at 3000 g for 5 minutes to remove cellular debris. Next, 200 µL of supernatant was lysed with 60 µL of lysis solution buffer plus 1 µg carrier-RNA. For normalization of sample-to-sample variation, 1 µL of synthetic *Caenorhabditis elegans* miRNA (cel-miR-39) was added to each denatured sample (18). Then, 20 µL of protein precipitation solution buffer was added and centrifuged for 3 minutes at 11000 g. Subsequently, 270 µL of isopropanol was added and centrifuged for 30 seconds at 11000 g as described previously (19). Small RNAs were then enriched and purified according to the manufacturer's protocol.

Real-time Polymerase Chain Reaction (RT-qPCR)

To optimize RT-qPCR performance, we did a dilution curve to determine what input volume affects RT-qPCR performance. Based on the outcome, 4µL of small RNAs from the biofluids samples were reverse transcribed using the miRCURY™ LNA Universal RT microRNA PCR protocol (Exiqon) in a total reaction volume of 10µL. The cDNA synthesis reaction was incubated at 42° C. for 60 minutes, followed by 95° C. for 5 minutes and the cDNA was diluted 1:40µL in nuclease free water to be used as a PCR template.

PCR reactions for quantification of miR-200a, miR-200b, miR-200c, miR-141, miR-429, miR-10a, and cell-miR-39 were performed in triplicate using New Exilent Syber Green master mix and 20µl was used as the reaction volume. The RT-qPCR reactions were performed using an ABI 7500 Real-Time PCR System with the following cycling conditions: 95° C. for 10 minutes, followed by 45 cycles of 95° C. for 10 seconds and 60° C. for 1 minute. The cycle threshold (Ct) values were calculated with ABI 7500 v1.4.0 software. The target microRNAs sequences of the LNA mix primers used were:

```
                                          (SEQ ID NO: 1)
UAACACUGUCUGGUAACGAUGU for hsa-miR-200a-3p, (SEQ ID NO: 2)
UAAUACUGCCUGGUAAUGAUGA for hsa-miR-200b-3p, (SEQ ID NO: 3)
UAAUACUGCCGGGUAAUGAUGGA for hsa-miR-200c-3p, (SEQ ID NO: 4)
UAACACUGUCUGGUAAAGAUGG for hsa-miR-141-3p, (SEQ ID NO: 5)
UAAUACUGUCUGGUAAAACCGU for hsa-miR-429, (SEQ ID NO: 6)
UACCCUGUAGAUCCGAAUUUGUG for hsa-miR-10a-5p,
and (SEQ ID NO: 7)
UCACCGGGUGUAAAUCAGCUUG for cel-miR-39-3p.
```

Calculation of miRNA Expression

The average expression levels of amniotic and tracheal fluid miRNAs were normalized against cel-miR-39(18, 20, 21) using the $2^{-\Delta Ct}$ method. Differences between the groups are presented as ΔCt, indicating the difference between the Ct value of the miRNA of interest and the Ct value of the normalizer miRNA. To ensure consistent measurements and reproducibility throughout all assays, for each PCR amplification reaction, one of the RNA samples was loaded in triplicate in all the plates, as internal control to account for any plate-to-plate variation, and the results from each plate were also normalized against an internal normalization control. The expression levels of microRNAs were normalized with the *C. Elegans* . cel-miR-39 Spike-in kit.

In Situ Hybridization

We obtained post-mortem neonatal lung tissues from three postnatal CDH cases and three age-matched controls, without lung disease (35, 37 and 40 weeks of gestation). All cases died within one hour after birth. In situ hybridization was carried out on 5 µm sections of formalin-fixed tissue as previously described (22). Our protocol was first validated with an LNA control probe against U6 snRNA. Optimal staining was achieved at 0.1 nM probe concentration, in accordance with the manufacturer's recommendations. A scramble-miR probe was used as a negative control and did not produce a signal. In situ hybridization with a probe against miR-10a produced a very weak signal in postnatal lung tissues. MicroRNA species were hybridized with double-digoxigenin-labeled LNA probes (Exiqon) for 1 hour (Table 2). We detected the hybridized probes with an alkaline phosphatase (AP)-conjugated anti-digoxigenin antibody (1:500) (Roche, Mannheim, Germany). Sections were immunostained with 1-step NBT/BCIP solution, containing 1 mM levamisole (Thermo Scientific, Rockford, Ill., USA). The slides were counterstained with methyl green (Sigma-Aldrich, St. Louis, Mo., USA).

Microscopy and Image Analysis

Digital microscopy was performed with the ScanScope CS system (Aperio, Vista, Calif., USA). Semi-quantitative measurements of the in situ hybridization studies were obtained as follows. Images were obtained up to 200× magnification and were analyzed using the ImageScope software. The entire area of each lung section was digitally mapped using the colocalization algorithm. The blue and green stains were first calibrated with the color deconvolution tool using positive (U6 probe without counterstain) and negative (scramble probe with methyl green counterstain) control slides, respectively. The average optical densities of each stain in the red, blue and green channels were then entered into the colocalization algorithm. The program creates a digital map of the slide made up of three colors: blue for positive staining, green for nuclear counterstaining and aqua for colocalized blue and green staining. This digital map was visually checked against the original image to ensure accuracy. The program outputs the area of each color as a percentage of all three colors. Positive staining was calculated by adding the percentages of blue and aqua (% positive staining).

Immunohistochemistry

We performed immunohistochemistry on neonatal lung tissue using an anti-TGF-β2 antibody (1:100) (Abcam, Cambridge, Mass., USA) as previously described (23). We also performed immunohistochemistry on rat lung tissue using an anti-ZEB2 antibody (Sigma-Aldrich, St. Louis, Mo., USA) and anti-TGF-82 antibody (Abcam, Cambridge, Mass., USA) as previously described (88).

Luciferase Assay

We used the Cignal SMAD Reporter kit (SABiosciences, Frederick, Md., USA) to investigate the effects of miR-200b on the TGF-β-induced signal transduction pathway (24). The construct encodes the firefly luciferase reporter gene under the control of a minimal (m)CMV promoter and tandem repeats of the SMAD transcriptional response element. The assay was carried out according to the manufacturer's instructions. Cultured human bronchial epithelial cells, BEAS-2B (ATCC, Manassas, Va., USA), were co-transfected with 0.5µg/ml of the SMAD reporter construct and 0.01 µg/ml of LNA-oligonucleotide—inhibitor, mimic or control (Exiqon)—using the X-tremeGENE siRNA Transfection Reagent (Roche). After 48 hours, luciferase activity was measured with the Dual-Luciferase Reporter Assay System (Promega, Madison, Wis., USA).

Western Blots

BEAS-2B cells were transfected with 0.01 µg/ml of LNA-oligonucleotide. After 48 hours the cells were washed and protein extracts were prepared in lysis buffer: 10 mM Tris-HCl (pH 6.8), 5 µM β-glycerophosphate, 20 µM EDTA, 5% SDS, a protease inhibitor cocktail tablet and phosphatase inhibitors (1 mM sodium orthovanadate, 2 mM EDTA, 10 mM sodium pyrophosphate, 30 mM sodium chloride). Following centrifugation (13 000×g, 10 min), the supernatant protein concentration was determined using RC DCTM Protein Assay (Bio-Rad, Hercules, Calif., USA). Fifteen micrograms of total protein was reduced with mercaptoethanol, size fractionated with SDS-PAGE and transferred to a nitrocellulose membrane (Bio-Rad). Specific proteins were detected with the following antibodies: anti-SMAD2/3 (1:750) (Cell Signaling, Danvers, Mass., USA), anti-phospho-SMAD2 (1:750) (Cell Signaling), anti-ZEB2 (1:500) (Santa Cruz Biotechnology, Santa Cruz, Calif., USA), and anti-GAPDH (1:10000) (Abcam). Primary antibodies were detected using HRP-conjugated goat-anti-rabbit antibody (1:7000) (Bio-Rad) and HRP-conjugated goat-anti-mouse antibody (1:7000) (Bio-Rad). Exposed films were scanned and band densities were obtained after background subtraction using ImageJ software in a blinded fashion. Band densities were normalized against the corresponding GAPDH values.

Ethical Approval and Animal Model

Sprague-Dawley rats were maintained in accordance with the guidelines of "Guide to the Care and Use of Experimental Animals". The Review Committee at the University of Manitoba approved the protocols for our current study. The animals were mated during the night cycle and the next day, after confirming vaginal plug, was considered as embryonic day zero (E0). In order to induce the CDH and pulmonary hypoplasia in rat fetus, 100 mg of nitrofen was dissolved in 1 ml olive oil and given to the dams by intragastrically on day 9 (73). In contrast, animals in the control group received only vehicle.

RNA Extraction and Real Time Quantitative PCR

Total RNA from embryonic lung tissues (nitrofen and control rats) or BEAS-2b cells (treated with 10 µM nitrofen or control) were extracted using the miRCURY™ Isolation Kit (Exiqon), according to the manufacturer's instructions. Subsequently, q-rtPCR analysis was performed using locked nucleotide acid (LNA) primer for mo-miR-200b and U6 (as a endogenous control) and miRCURY LNA™ Universal RT microRNA PCR and SYBR® Green Master Mix kits (Exiqon).

In Situ Hybridization and Combined In Situ Hybridization-Immunohistochemistry (ISH/IHC)

Lung tissues from different stages of lung development were isolated and embedded in paraffin. In situ hybridization was carried out on 5 µm tissue sections as previously described (22). Rno-LNA-miR-200b were hybridized with double-digoxigenin-labeled LNA probes (Exiqon) for 1 hour at 52° C. (30° C. below the calculated RNA melting temperature). The probes were detected with an alkaline phosphatase (AP)-conjugated anti-digoxigenin antibody (Roche, Mannheim, Germany). Sections were immunostained with 1-step NBT/BCIP solution, containing 1 mM levamisole (Thermo Scientific, Rockford, Ill., USA). The slides were then counterstained with methyl green (Sigma-Aldrich, St. Louis, Mo., USA). Digital microscopy was performed with the ScanScope CS system (Aperio, Vista, Calif., USA). Semi-quantitative measurements of immunostaining were obtained. For combined ISH/IHC, we performed with ISH experiment, after immunostaining the sections with 1-step NBT/BCIP solution; we then proceed with IHC assay applying the blocking solution.

Luciferase Activity Assay Human bronchial epithelial cells, BEAS-26 (ATCC, Manassas, Va., USA), were treated with 10 µM of nitrofen, after one hour of incubation, treated or untreated cells co-transfected with 0.5 µg/ml of the SMAD reporter construct (Cignal SMAD Reporter kit, SABiosciences, Frederick, Md., USA) (24) and 0.01 µg/ml of LNA-has-miR-200b inhibitor, mimic or negative control (Exiqon)—using the X-tremeGENE siRNA Transfection Reagent (Roche). After 48 hours, luciferase activity was measured with the Dual-Luciferase Reporter Assay System (Promega, Madison, Wis., USA) using a core BMG POLARstar OPTIMA Microplate Reader.

Western Blotting

Nitrofen treated or untreated BEAS-2B cells were transfected with 0.01 µg/ml of LNA-hsa-miR-200b inhibitor, mimic or negative control. After 48 hours, immunoblotting was carried out.

Statistical Analysis

Some data are presented as mean+/−standard deviation, from three independent experiments. To determine statistical significance, Student's t-test (two-tailed) was used on these data to compare two groups. A p-value of less than 0.05 was considered significant. All quantitative data are presented as mean±SEM or median and IQR where appropriate. Statistical analyses were performed using the statistical software SigmaStat (version 3.5; Systat Software Inc., USA). Statistical comparisons were performed using the unpaired Student's t test and non-parametric Mann-Whitney-U test where appropriate. Paired analysis was performed using a Wilcoxon signed rank test. Differences were considered significant at P<0.05.

Fetal Lung Explant Cultures

Lung tissues from E13 nitrofen treated and control embryos were harvested using a stereomicroscope (Leica MZ6, Switzerland). We designed the experiment in 4 different groups: Control lungs incubated with oligo negative control, miR-200b inhibitor or miR-200b mimic and Nitrofen lungs incubated with miR-200b mimic. Three lungs per group were incubated in 200 µl media (1:1 mixture of DMEM and Ham's F-12 Nutrient supplemented with 100 µg/ml streptomycin, 100 units/ml penicillin, 0.25 mg/ml ascorbic acid (Sigma-Aldrich, USA) containing 200 nM oligomers for one hour. Then media and lungs were transferred to porous membranes (Isopore™ membrane filters with dimensions of 1 mm×1.5 mm pore size, Millipore, USA) in a 12-well plate to enable semi-dry lung explant culture. Branching morphogenesis and epithelial perimeter in all groups were monitored daily by stereomicroscope. The differences between day 0 (D0: 0 hours) and day 4 (D4: 96 hours) of culture, were expressed as D4/ D0 ratio.

MiR-200b Knockout Mouse Studies

Figure 10:
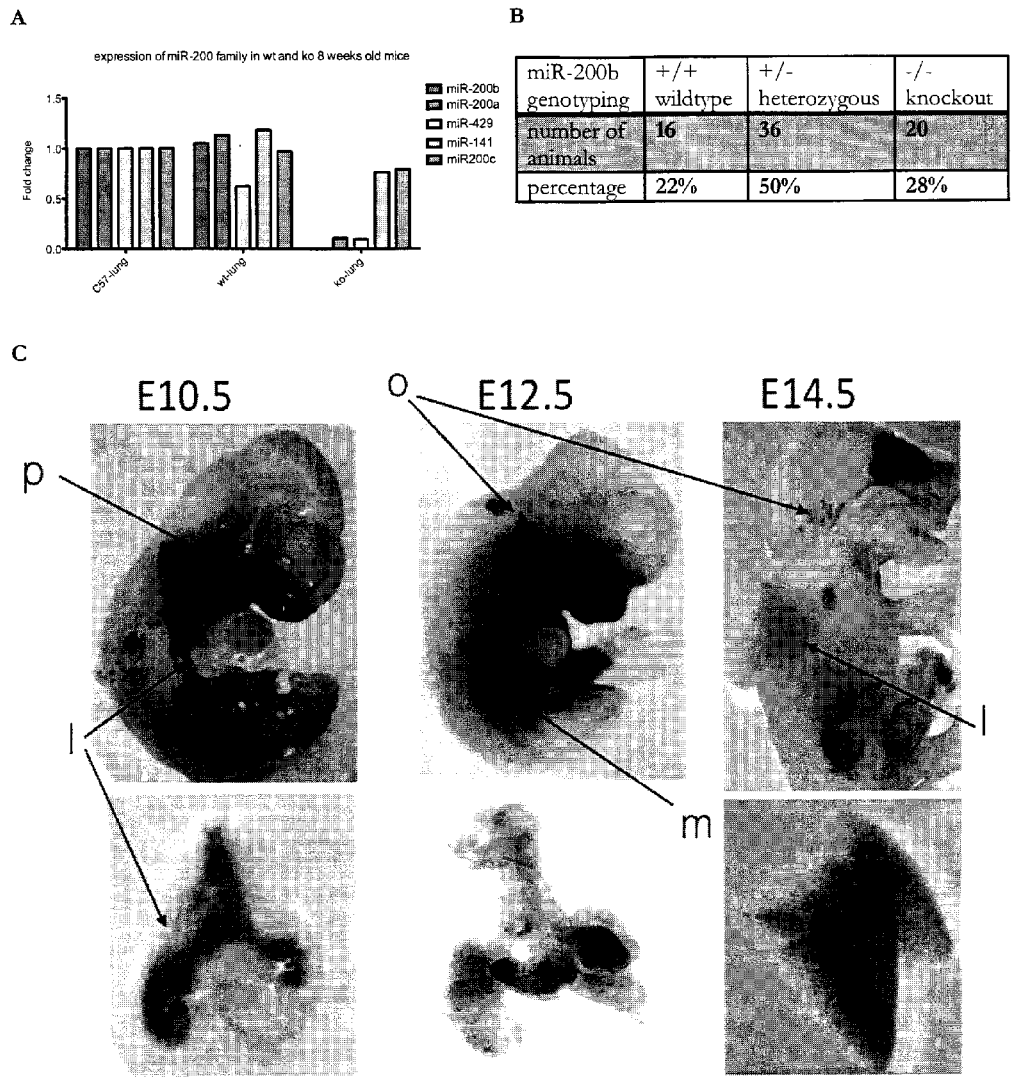
FIG. 10. Establishment of our miR-200b knockout mouse. (A) RT-qPCR confirms the absence of miR-200b expression in lungs of our miR-200b knockout mice. (B) We observed a Mendelian distribution of offspring from heterozygous miR-200b+/−crosses. (C) E10.5, E12.5 and E14.5 whole mount miR-200b-lacZ+/-expression (blue) is observed in the lungs (l), palate (p), otic vesicle (o) and mammary buds (m). Dynamic expression between the lung endoderm (E10.5), lung mesenchyme (E12.5) and lung epithelium (E14.5) is observed at the bottom in explanted lungs.

We confirmed complete miR-200b knockout and showed that microRNAs transcribed in the same cluster—miR-200a and miR-429—were still expressed (FIG. 10A). In addition, all genotyping results demonstrated a predicted Mendelian distribution, indicating that these mice experience no embryonic lethality (FIG. 10B).

Figure 11:
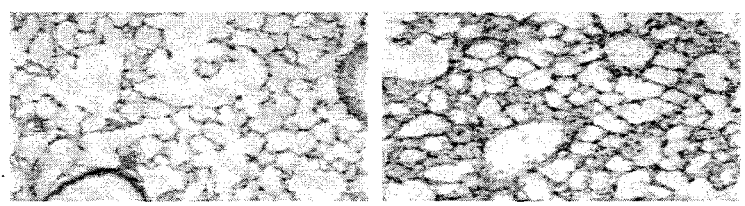
FIG. 11. MiR-200b−/−mice have significant less compliant lungs. Lung function studies in 8-weeks-old knockout mice show significantly increased tissue damping and elastance (A-D). This suggests peripheral lung stiffness and changes in small peripheral airway resistance. Surfactant content was also reduced in the knockout lungs (E). Finally, sections of the lungs showed that knockout mice had thicker alveolar walls and less distal airway branching (G). *P<0.05, P<0.01, *P<0.001. Two-way ANOVA (number of replicates are four).
Figure 11A:
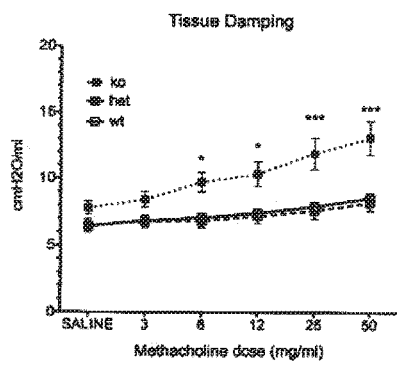
Figure 11B:
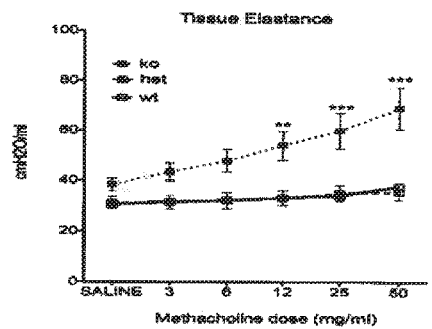
Figure 11C:
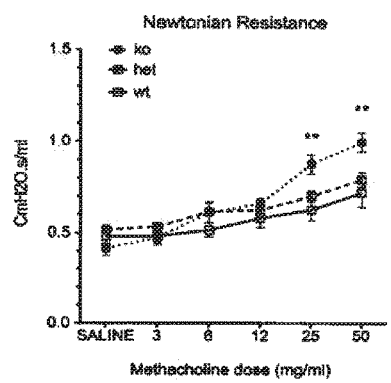
Figure 11D:
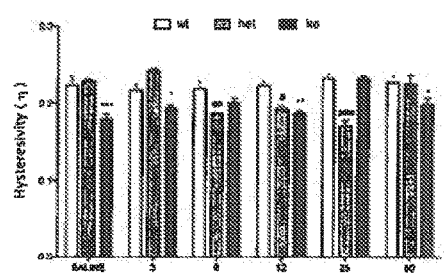
Figure 11E:
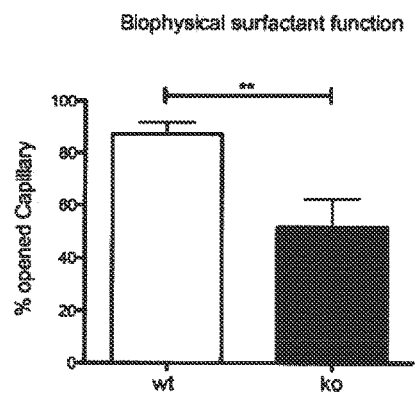

In contrast to miR-200b/miR-429 double transgenic mice reported by others, our miR-200b transgenic mice carry a lacZ-reporter gene (FIG. 10C) allowing us to localize miR-200b absence during development and prioritize the phenotyping of these mice. Of particular interest to this proposal, we observed a high and dynamic expression in the endoderm of the foregut and lung buds (FIG. 10C). Expression started in the lung bud endoderm at E10.5, switched to the mesenchyme at E12.5 during branching morphogenesis and then reverted back to the endoderm of the airways at E14.5 (FIG. 11C). Additionally, we observed high LacZ-miR-200b expression in organs where development also hinges on epithelial-mesenchymal interactions. These organs include the developing inner ear, palate and mammary buds (FIG. 11O), consistent with prior reports indicating that miR-200b controls the development of these organs.

MiR-200b Knockout Mice Have Less Compliant Lungs

To determine whether lung function is affected in adult miR-200b mutant mice, we used the flex/VENT small animal ventilator core facility at our institute to perform lung function analyses. These studies were performed on 8-week old miR-200b−/−mice, and we compared their lung function to miR-200+/+mice. We found that miR-200b−/−mice have a higher lung tissue resistance or damping, as well as higher tissue elastance (FIG. 11). Methacholine challenge magnified these differences. In contrast, central airway resistance was not different. Surfactant content was also reduced in the knockout lungs (E). Finally, sections of the lungs showed that knockout mice had thicker alveolar walls and less distal airway branching (G).

The scope of the claims should not be limited by the preferred embodiments set forth in the examples, but should be given the broadest interpretation consistent with the description as a whole.

REFERENCES

1. Langham M R, Kays D W, Ledbetter D J, Frentzen B, Sanford L L, Richards D S. Congenital diaphragmatic hernia. Epidemiology and outcome. Clin Perinatol. 1996 December; 23(4):671-88.

2. Jani J C, Nicolaides K H, Gratacos E, Valencia C M, Doné E, Martinez J-M, et al. Severe diaphragmatic hernia treated by fetal endoscopic tracheal occlusion. Ultrasound Obstet Gynecol. 2009 September; 34(3):304-10.

7. Veenma D C M, de Klein a, Tibboel D. Developmental and genetic aspects of congenital diaphragmatic hernia. Pediatr Pulmonol. 2012 June; 47(6):534-45.

8. Keijzer R, Liu J, Deimling J, Tibboel D, Post M. Dual-hit hypothesis explains pulmonary hypoplasia in the nitrofen model of congenital diaphragmatic hernia. Am J Pathol. American Society for Investigative Pathology; 2000 April; 156(4):1299-306.

9. Allan D W, Greer J J. Pathogenesis of nitrofen-induced congenital diaphragmatic hernia in fetal rats. J Appl Physiol. 1997 August; 83(2):338-47.

10. Ambros V. The functions of animal microRNAs. Nature. 2004 Sep. 16; 431(7006):350-5.

11. Zhao Y, Ransom J F, Li A, Vedantham V, von Drehle M, Muth A N, et al. Dysregulation of cardiogenesis, cardiac conduction, and cell cycle in mice lacking miRNA-1-2. Cell. 2007 Apr. 20; 129(2):303-17.

12. Mujahid S, Logvinenko T, Volpe M V, Nielsen H C. miRNA regulated pathways in late stage murine lung development. BMC Dev Biol. 2013 January; 13(1):13.

13. Metkus A P, Filly R A, Stringer M D, Harrison M R, Adzick N S. Sonographic predictors of survival in fetal diaphragmatic hernia. J Pediatr Surg. 1996 January; 31(1):148-51; discussion 151-2.

14. Jani J, Nicolaides K H, Keller R L, Benachi a, Peralta C F a, Favre R, et al. Observed to expected lung area to head circumference ratio in the prediction of survival in fetuses with isolated diaphragmatic hernia. Ultrasound Obstet Gynecol. 2007 July; 30(1):67-71.

15. Done E, Allegaert K, Lewi P, Jani J, Gucciardo L, Van Mieghem T, et al. Maternal hyperoxygenation test in fetuses undergoing FETO for severe isolated congenital diaphragmatic hernia. Ultrasound Obstet Gynecol. 2011 March; 37(3):264-71.

16. DeKoninck P, Lewi P, Done E, Richter J, Gucciardo L, Van Mieghem T, et al. Sonographic evaluation of vascular pulmonary reactivity following oxygen administration in fetuses with normal lung development. Prenat Diagn. 2012 December; 32(13):1300-4.

17. Cannie M M, Jani J C, De Keyzer F, Allegaert K, Dymarkowski S, Deprest J. Evidence and patterns in lung response after fetal tracheal occlusion: clinical controlled study. Radiology. 2009 August; 252(2):526-33.

18. Argyropoulos C, Wang K, McClarty S, Huang D, Bernardo J, Ellis D, et al. Urinary microRNA profiling in the nephropathy of type 1 diabetes. PLoS One. 2013 January; 8(1):e54662.

19. Mitchell P S, Parkin R K, Kroh E M, Fritz B R, Wyman S K, Pogosova-Agadjanyan E L, et al. Circulating microRNAs as stable blood-based markers for cancer detection. Proc Natl Acad Sci USA. 2008 Jul. 29; 105(30):10513-8.

20. Kroh E M, Parkin R K, Mitchell P S, Tewari M. Analysis of circulating microRNA biomarkers in plasma and serum using quantitative reverse transcription-PCR (qRT-PCR). Methods. Elsevier Inc.; 2010 April; 50(4):298-301.

21. Weber J a, Baxter D H, Zhang S, Huang D Y, Huang K H, Lee M J, et al. The microRNA spectrum in 12 body fluids. Clin Chem. 2010 November; 56(11):1733-41.

22. Jorgensen S, Baker A, Moller S, Nielsen B S. Robust one-day in situ hybridization protocol for detection of microRNAs in paraffin samples using LNA probes. Methods. 2010 December; 52(4):375-81.

24. Leeper N J, Raiesdana A, Kojima Y, Chun H J, Azuma J, Maegdefessel L, et al. MicroRNA-26a is a novel regulator of vascular smooth muscle cell function. J Cell Physiol. 2011 April; 226(4):1035-43.

25. Evrard V a, Flageole H, Deprest J a, Vandenberghe K, Verhaeghe J, Lerut T E. Intrauterine tracheal obstruction, a new treatment for congenital diaphragmatic hernia, decreases amniotic fluid sodium and chloride concentrations in the fetal lamb. Ann Surg. 1997 December; 226(6):753-8.

26. Burk U, Schubert J, Wellner U, Schmalhofer O, Vincan E, Spaderna S, et al. A reciprocal repression between ZEB1 and members of the miR-200 family promotes EMT and invasion in cancer cells. EMBO Rep. 2008 June; 9(6): 582-9.

27. Xu J, Lamouille S, Derynck R. TGF-beta-induced epithelial to mesenchymal transition. Cell Res. 2009 February; 19(2):156-72.

29. Gregory P a, Bert A G, Paterson E L, Barry S C, Tsykin A, Farshid G, et al. The miR-200 family and miR-205 regulate epithelial to mesenchymal transition by targeting ZEB1 and SIP1. Nat Cell Biol. 2008 May; 10(5):593-601.

32. Park S-M, Gaur A B, Lengyel E, Peter M E. The miR-200 family determines the epithelial phenotype of cancer cells by targeting the E-cadherin repressors ZEB1 and ZEB2. Genes Dev. 2008 Apr. 1; 22(7):894-907.

33. Gregory P a, Bracken C P, Smith E, Bert A G, Wright J a, Roslan S, et al. An autocrine TGF-beta/ZEB/miR-200 signaling network regulates establishment and maintenance of epithelial-mesenchymal transition. Mol Biol Cell. 2011 May 15; 22(10):1686-98.

34. Kato M, Arce L, Wang M, Putta S, Lanting L, Natarajan R. A microRNA circuit mediates transforming growth factor-β1 autoregulation in renal glomerular mesangial cells. Kidney Int. Nature Publishing Group; 2011 August; 80(4):358-68.

35. Quinn T M, Sylvester K G, Kitano Y, Liechty K W, Jarrett B P, Adzick N S, et al. TGF-beta2 is increased after fetal tracheal occlusion. J Pediatr Surg. 1999 May; 34(5): 701-4; discussion 704-5.

36. Oue T, Shima H, Taira Y, Puri P. Administration of antenatal glucocorticoids upregulates peptide growth factor gene expression in nitrofen-induced congenital diaphragmatic hernia in rats. J Pediatr Surg. 2000 January; 35(1): 109-12.

37. Yamataka T, Puri P. Active collagen synthesis by pulmonary arteries in pulmonary hypertension complicated by congenital diaphragmatic hernia. J Pediatr Surg. 1997 May; 32(5):682-7.

38. Teramoto H, Shinkai M, Puri P. Altered expression of angiotensin II receptor subtypes and transforming growth factor-beta in the heart of nitrofen-induced diaphragmatic hernia in rats. Pediatr Surg Int. 2005 March; 21(3):148-52.

46. Pechkovsky D V, Hackett T L, An S S, Shaheen F, Murray L a, Knight D a. Human lung parenchyma but not proximal bronchi produces fibroblasts with enhanced TGF-beta signaling and alpha-SMA expression. Am J Respir Cell Mol Biol. 2010 December; 43(6):641-51.

47. Bragg a D, Moses H L, Serra R. Signaling to the epithelium is not sufficient to mediate all of the effects of transforming growth factor beta and bone morphogenetic protein 4 on murine embryonic lung development. Mech Dev. 2001 November; 109(1):13-26.

48. Chen H, Zhuang F, Liu Y-H, Xu B, Del Moral P, Deng W, et al. TGF-beta receptor II in epithelia versus mesenchyme plays distinct roles in the developing lung. Eur Respir J Off J Eur Soc Clin Respir Physiol. 2008 August; 32(2): 285-95.

49. Lund a H. miR-10 in development and cancer. Cell Death Differ. Nature Publishing Group; 2010 February; 17(2):209-14.

52. Huang H, Xie C, Sun X, Ritchie R P, Zhang J, Chen Y E. miR-10a contributes to retinoid acid-induced smooth muscle cell differentiation. J Biol Chem. 2010 Mar. 26; 285(13):9383-9.

53. Andersen D H. Incidence of congenital diaphragmatic hernia in the young of rats bred on a diet deficient in vitamin A. Am J Dis Child. 1941; 62:888-9.

54. Mendelsohn C, Lohnes D, Decimo D, Lufkin T, LeMeur M, Chambon P, et al. Function of the retinoic acid receptors (RARs) during development (II). Multiple abnormalities at various stages of organogenesis in RAR double mutants. Development. 1994 October; 120(10):2749-71.

55. Wilson J G, Roth C B, Warkany J. An analysis of the syndrome of malformations induced by maternal vitamin A deficiency. Effects of restoration of vitamin A at various times during gestation. Am J Anat. 1953 March; 92(2):189-217.

56. Beurskens L W J E, Tibboel D, Lindemans J, Duvekot J J, Cohen-Overbeek T E, Veenma D C M, et al. Retinol status of newborn infants is associated with congenital diaphragmatic hernia. Pediatrics. 2010 October; 126(4):712-20.

57. Toiyama Y, Hur K, Tanaka K, Inoue Y, Kusunoki M, Boland C R, et al. Serum miR-200c Is a Novel Prognostic and Metastasis-Predictive Biomarker in Patients With Colorectal Cancer. Ann Surg. 2013 Aug. 26; 00(00):1-9.

58. Valladares-Ayerbes M, Reboredo M, Medina-Villaamil V, Iglesias-Diaz P, Lorenzo-Patiño M J, Haz M, et al. Circulating miR-200c as a diagnostic and prognostic biomarker for gastric cancer. J Transl Med. 2012 January; 10:186.

59. Hu X, Macdonald D M, Huettner P C, Feng Z, El Naga I M, Schwarz J K, et al. A miR-200 microRNA cluster as prognostic marker in advanced ovarian cancer. Gynecol Oncol. Elsevier Inc.; 2009 September; 114(3):457-64.

60. Ohuchida K, Mizumoto K, Lin C, Yamaguchi H, Ohtsuka T, Sato N, et al. MicroRNA-10a is overexpressed in human pancreatic cancer and involved in its invasiveness partially via suppression of the HOXA1 gene. Ann Surg Oncol. 2012 July; 19(7):2394-402.

61. Santarpia L, Calin G a, Adam L, Ye L, Fusco A, Giunti S, et al. A miRNA signature associated with human metastatic medullary thyroid carcinoma. Endocr Relat Cancer. 2013 December; 20(6):809-23.

62. Köhler C U, Bryk O, Meier S, Lang K, Rozynek P, Brüning T, et al. Analyses in human urothelial cells identify methylation of miR-152, miR-200b and miR-10a genes as candidate bladder cancer biomarkers. Biochem Biophys Res Commun. Elsevier Inc.; 2013 Aug. 16; 438(1):48-53.

63. Gallot D, Boda C, Ughetto S, Perthus I, Robert-Gnansia E, Francannet C, et al. Prenatal detection and outcome of congenital diaphragmatic hernia: a French registry-based study. Ultrasound Obstet Gynecol. 2007 March; 29(3):276-83.

67. Wynn, J. et al. Outcomes of Congenital Diaphragmatic Hernia in the Modern Era of Management. J Pediatr (2013). doi:S0022-3476(12)01525-9 [pii] 10.1016/j.jpeds.2012.12.036

68. Wright, J. C., Budd, J. L., Field, D. J. & Draper, E. S. Epidemiology and outcome of congenital diaphragmatic hernia: a 9-year experience. Paediatr Perinat Epidemiol 25,144-149 (2011).

69. Gischler, S. J. et al. A prospective comparative evaluation of persistent respiratory morbidity in esophageal atresia and congenital diaphragmatic hernia survivors. J Pediatr Surg 44, 1683-1690 (2009).

70. Van Loenhout, R. B., Tibboel, D., Post, M. & Keijzer, R. Congenital diaphragmatic hernia: comparison of animal models and relevance to the human situation. Neonatology 96, 137-149 (2009).

71. Pober, B. R. et al. Infants with Bochdalek diaphragmatic hernia: sibling precurrence and monozygotic twin discordance in a hospital-based malformation surveillance program. Am. J. Med. Genet. A 138A, 81-8 (2005).

72. Pober, B. R. Genetic aspects of human congenital diaphragmatic hernia. Clin. Genet. 74, 1-15 (2008).

75. Sayed, D. & Abdellatif, M. MicroRNAs in development and disease. Physiol Rev 91, 827-887 (2011).

76. Brabletz, S. & Brabletz, T. The ZEB/miR-200 feedback loop—a motor of cellular plasticity in development and cancer? EMBO Rep 11, 670-677 (2010).

77. Howe, E. N., Cochrane, D. R. & Richer, J. K. The miR-200 and miR-221/222 microRNA families: opposing effects on epithelial identity. J Mammary Gland Biol Neoplasia 17, 65-77 (2012).

78. Kurashige, J. et al. MicroRNA-200b regulates cell proliferation, invasion, and migration by directly targeting ZEB2 in gastric carcinoma. Ann Surg Oncol 19 Suppl 3, S656-64 (2012).

79. Yang, S. et al. Participation of miR-200 in pulmonary fibrosis. Am J Pathol 180, 484-493 (2012).

80. Rawlins, E. L., Clark, C. P., Xue, Y. & Hogan, B. L. The Id2+ distal tip lung epithelium contains individual multipotent embryonic progenitor cells. Development 136, 3741-3745 (2009).

81. Wang, G. et al. Critical regulation of miR-200/ZEB2 pathway in Oct4/ Sox2-induced mesenchymal-to-epithelial transition and induced pluripotent stem cell generation. Proc Natl Acad Sci USA 110, 2858-2863 (2013).

82. Kong, D. et al. miR-200 regulates PDGF-D-mediated epithelial-mesenchymal transition, adhesion, and invasion of prostate cancer cells. Stem Cells 27, 1712-1721 (2009).

83. Torday, J. & Rehan, V. Neutral lipid trafficking regulates alveolar type II cell surfactant phospholipid and surfactant protein expression. Exp. Lung Res. 37, 376-386 (2011).

84. Watanabe, Y. et al. Amniotic lamellar body count and congenital diaphragmatic hernia in humans and in a rat model. Pediatr. Res. 73, 344-8 (2013).

85. Cogo, P. E. et al. Impaired surfactant protein B synthesis in infants with congenital diaphragmatic hernia. Eur. Respir. J. 41, 677-82 (2013).

86. Xiong, M. et al. The miR-200 family regulates TGF-beta1-induced renal tubular epithelial to mesenchymal transition through Smad pathway by targeting ZEB1 and ZEB2 expression. Am J Physiol Ren. Physiol 302, F369-79 (2012).

87. Kim, S. W. et al. A sensitive non-radioactive northern blot method to detect small RNAs. Nucleic Acids Res. 38, e98 (2010).

88. Chi, V. & Chandy, K. G. Immunohistochemistry: paraffin sections using the Vectastain ABC kit from vector labs. J. Vis. Exp. 308 (2007). doi:10.3791/308

89. Liang, C.-C., Park, A. Y. & Guan, J.-L. In vitro scratch assay: a convenient and inexpensive method for analysis of cell migration in vitro. Nat. Protoc. 2, 329-333 (2007).

93. Bracken C P, Gregory P A, Kolesnikoff N, et al: A double-negative feedback loop between ZEB1-SIP1 and the microRNA-200 family regulates epithelial-mesenchymal transition. Cancer Res 68: 7846-7854, 2008.

TABLE 1

LNA primer sets (Exigon) used in real-time quantitative polymerase chain reaction (gPCR)

| LNA microRNA primer set | Description |
|---|---|
| SNORD38B | Endogenous control |
| 5S rRNA (hsa) | Endogenous control |
| U6 snRNA (hsa, mmu) | Endogenous control |
| hsa-miR-10a | Tested microRNA |
| hsa-miR-27a | Tested microRNA |
| hsa-miR-195 | Tested microRNA |
| hsa-let-7a | Tested microRNA |
| hsa-miR-1 | Tested microRNA |
| hsa-miR-200b | Tested microRNA |

TABLE 2

LNA probes (Exiqon) used for in situ hybridization

| Probe | Sequence | Concentration | Hybridization Temperature |
|---|---|---|---|
| hsa-miR-200b human (SEQ ID NO: 8) | TCATCATTACCAGGCAGTATTA | 100 nM | 52° C. |
| hsa-miR-10a human (SEQ ID NO: 9) | CACAAATTCGGATCTACAGGGTA | 100 nM | 53° C. |
| Scramble-miR negative control (SEQ ID NO: 10) | GTGTAACACGTCTATACGCCCA | 100 nM | 57° C. |
| U6 positive control (SEQ ID NO: 11) | CACGAATTTGCGTGTCATCCTT | 0.1 nM | 54° C. |

TABLE 3

Base-line characteristics of the embryos.

| Characteristics | Responders (n = 11) | Non-responders (n = 10) | P value |
|---|---|---|---|
| O/E LHR at first evaluation (%) | 22.5 (23.6-17.5) | 21.6 (24.0-15.9) | 0.87 |
| Liver herniated | 10 (91%) | 9 (100%) | 1.00 |
| Fetal gender (male/female) | 7(m)/4(f) | 4(m)/5(f) | 0.65 |

TABLE 4

FETO pregnancy data and neonatal outcome.

| FETO data/outcome | Responders (n = 11) | Non-responders (n = 10) | P Value |
|---|---|---|---|
| Gestational age at plug (wk) | 28.1 (28.7-27.1) | 27.9 (29.1-27.0) | 0.84 |
| Gestational age at unplug (wk) | 34.0 (34.1-33.4) | 34 (34.5-33.9) | 0.36 |
| Occlusion days | 39 (49-35) | 43 (50-34) | 0.64 |
| Relative increase O/E LHR | 161.7 (252.4-140.8) | 29.8 (10.4-50.2) | <0.0001 |
| Interval removal-delivery <24 h | 1 (9%) | 0 (0%) | 1.00 |
| PPROM | 5 (45%) | 3 (33%) | 0.67 |
| Gestational age at PPROM (wk) | 35.0 (35.9-32.6) | 35.4 (36.6-29.3) | 1.00 |
| Gestational age at delivery (wk) | 37.0 (38.0-35.0) | 38.0 (38.4-36.4) | 0.25 |
| Birth weight (g) | 2780 (3180-2160) | 3195 (3278-2650) | 0.30 |
| Oxygen at day 28 | 6 (55%) | n.a. | |
| NICU days | 45 (61-30) | n.a. | |
| Day of neonatal death | n.a. | 1 (2-0) | |

The invention claimed is:

1. A method of treating or preventing abnormal lung development in Congenital Diaphragmatic Hernia (CDH} comprising of:
   administering to an individual at risk of having abnormal lung development an effective amount of an miR-200b mimic compound.

2. The method according to claim 1 wherein the miR-200b mimic is a non-natural double stranded microRNA-like RNA fragment with a 5complementary sequence to the 3UTR unique to the target gene.

3. The method according to claim 1 wherein the miR-200b mimic compound is delivered intravenously, intra-amniotic, intratracheal or intranasal.

* * * * *

SEQUENCE LISTING

<160> NUMBER OF SEQ ID NOS: 11

<210> SEQ ID NO 1
<211> LENGTH: 22
<212> TYPE: RNA
<213> ORGANISM: artificial
<220> FEATURE:
<223> OTHER INFORMATION: primer

<400> SEQUENCE: 1
uaacacuguc ugguaacgau gu                22

<210> SEQ ID NO 2
<211> LENGTH: 22
<212> TYPE: RNA
<213> ORGANISM: artificial
<220> FEATURE:
<223> OTHER INFORMATION: primer

<400> SEQUENCE: 2
uaauacugcc ugguaaugau ga                22

<210> SEQ ID NO 3
<211> LENGTH: 23
<212> TYPE: RNA
<213> ORGANISM: artificial
<220> FEATURE:
<223> OTHER INFORMATION: primer

<400> SEQUENCE: 3
uaauacugcc ggguaaugau gga               23

<210> SEQ ID NO 4
<211> LENGTH: 22
<212> TYPE: RNA
<213> ORGANISM: artificial
<220> FEATURE:
<223> OTHER INFORMATION: primer

<400> SEQUENCE: 4
uaacacuguc ugguaaagau gg                22

<210> SEQ ID NO 5
<211> LENGTH: 22
<212> TYPE: RNA
<213> ORGANISM: artificial
<220> FEATURE:
<223> OTHER INFORMATION: primer

<400> SEQUENCE: 5

```
uaauacuguc ugguaaaacc gu                                             22

<210> SEQ ID NO 6
<211> LENGTH: 23
<212> TYPE: RNA
<213> ORGANISM: artificial
<220> FEATURE:
<223> OTHER INFORMATION: primer

<400> SEQUENCE: 6
uacccuguag auccgaauuu gug                                            23

<210> SEQ ID NO 7
<211> LENGTH: 22
<212> TYPE: RNA
<213> ORGANISM: artificial
<220> FEATURE:
<223> OTHER INFORMATION: primer

<400> SEQUENCE: 7
ucaccgggug uaaaucagcu ug                                             22

<210> SEQ ID NO 8
<211> LENGTH: 22
<212> TYPE: DNA
<213> ORGANISM: artificial
<220> FEATURE:
<223> OTHER INFORMATION: probe

<400> SEQUENCE: 8
tcatcattac caggcagtat ta                                             22

<210> SEQ ID NO 9
<211> LENGTH: 23
<212> TYPE: DNA
<213> ORGANISM: artificial
<220> FEATURE:
<223> OTHER INFORMATION: probe

<400> SEQUENCE: 9
cacaaattcg gatctacagg gta                                            23

<210> SEQ ID NO 10
<211> LENGTH: 22
<212> TYPE: DNA
<213> ORGANISM: artificial
<220> FEATURE:
<223> OTHER INFORMATION: probe

<400> SEQUENCE: 10
gtgtaacacg tctatacgcc ca                                             22

<210> SEQ ID NO 11
<211> LENGTH: 22
<212> TYPE: DNA
<213> ORGANISM: artificial
<220> FEATURE:
<223> OTHER INFORMATION: probe

<400> SEQUENCE: 11
cacgaatttg cgtgtcatcc tt                                             22
```